United States Patent
Olsson et al.

(10) Patent No.: US 10,379,436 B1
(45) Date of Patent: Aug. 13, 2019

(54) SPRING ASSEMBLIES WITH VARIABLE FLEXIBILITY FOR USE WITH PUSH-CABLES AND PIPE INSPECTION SYSTEMS

(71) Applicant: SeeScan Inc., San Diego, CA (US)

(72) Inventors: Mark S. Olsson, La Jolla, CA (US); Eric M. Chapman, San Diego, CA (US); James F. Kleyn, Santee, CA (US)

(73) Assignee: SEESCAN, INC., San Diego, CA (US)

(*) Notice: Subject to any disclaimer, the term of this patent is extended or adjusted under 35 U.S.C. 154(b) by 0 days.

(21) Appl. No.: 15/811,264

(22) Filed: Nov. 13, 2017

Related U.S. Application Data

(63) Continuation of application No. 15/296,018, filed on Oct. 7, 2016, now Pat. No. 9,829,783, which is a (Continued)

(51) Int. Cl.
*G03B 37/00* (2006.01)
*F16F 15/134* (2006.01)
(Continued)

(52) U.S. Cl.
CPC ............ *G03B 37/005* (2013.01); *F16F 3/04* (2013.01); *F16F 15/12346* (2013.01);
(Continued)

(58) Field of Classification Search
CPC ......... H04N 2005/2255; G01N 21/954; F16F 15/12346; F16F 15/13461; F16F 3/04;
(Continued)

(56) References Cited

U.S. PATENT DOCUMENTS

| 1,751,415 A | 3/1930 | McCaffrey |
| 1,863,460 A | 6/1932 | Auringer |

(Continued)

FOREIGN PATENT DOCUMENTS

| GB | 387250 | 2/1933 |
| JP | 2012132970 A | * 7/2012 |

OTHER PUBLICATIONS

International Searching Authority, "Written Opinion of the International Searching Authority" for PCT Patent Application No. PCT/US14/37020, dated Nov. 7, 2015, European Patent Office, Munich.

(Continued)

*Primary Examiner* — John Villecco
(74) *Attorney, Agent, or Firm* — Steven C. Tietsworth, Esq.; Heena Sharma

(57) ABSTRACT

Push-cables and associated apparatus and systems are disclosed. In one embodiment, a push-cable assembly for use with a pipe inspection system may include a push-cable element having a proximal end and a distal end, with a spring assembly having varying flexibility coupled to or near the distal end. The spring assembly may include an outer coiled spring having a proximal and a distal end, and an inner coiled spring nested at least partially within the outer coiled spring. A camera head and/or other elements such as a cutting or jetting apparatus may be coupled at or near the distal end.

9 Claims, 25 Drawing Sheets

Related U.S. Application Data continuation of application No. 14/271,255, filed on May 6, 2014, now Pat. No. 9,477,147.

(60) Provisional application No. 61/984,029, filed on Apr. 24, 2014, provisional application No. 61/820,640, filed on May 7, 2013.

(51) Int. Cl.
| | |
|---|---|
| *F16F 15/123* | (2006.01) |
| *F16F 3/04* | (2006.01) |
| *G02B 23/24* | (2006.01) |
| *G01N 21/954* | (2006.01) |
| *H04N 5/225* | (2006.01) |
| *B08B 9/043* | (2006.01) |
| *E03F 9/00* | (2006.01) |

(52) U.S. Cl.
CPC ..... *F16F 15/13461* (2013.01); *G01N 21/954* (2013.01); *G02B 23/2484* (2013.01); *B08B 9/0436* (2013.01); *E03F 9/00* (2013.01); *H04N 2005/2255* (2013.01)

(58) Field of Classification Search
CPC ..... F16F 3/06; G03B 37/005; G02B 23/2484; G02B 23/2492
See application file for complete search history.

(56) References Cited

U.S. PATENT DOCUMENTS

| | | | | |
|---|---|---|---|---|
| 2,608,421 | A | | 8/1952 | Schnepp |
| 2,880,435 | A | | 4/1959 | Deutsch et al. |
| 3,457,580 | A | * | 7/1969 | Meyers ............ F28G 3/12 15/104.33 |
| 5,052,404 | A | * | 10/1991 | Hodgson ........... A61M 25/005 267/155 |
| 5,060,660 | A | * | 10/1991 | Gambale ......... A61M 25/0144 600/585 |
| 5,165,421 | A | * | 11/1992 | Fleischhacker ... A61B 17/3207 138/130 |
| 5,306,252 | A | * | 4/1994 | Yutori ............ A61M 25/005 138/130 |
| 5,457,288 | A | * | 10/1995 | Olsson ................. H01B 7/183 174/105 R |
| 5,862,561 | A | * | 1/1999 | Irwin ................. B08B 9/045 134/113 |
| 6,862,945 | B2 | * | 3/2005 | Chapman ............. F16L 55/26 73/865.8 |
| 6,958,767 | B2 | * | 10/2005 | Olsson ................. H04N 7/185 348/82 |
| 7,347,754 | B1 | * | 3/2008 | Cheung ............ B63B 35/7906 441/65 |
| 8,984,698 | B1 | * | 3/2015 | Olsson ................. B08B 9/045 15/104.03 |
| 9,477,147 | B2 | * | 10/2016 | Chapman ............... F16C 1/10 |
| 9,829,783 | B1 | * | 11/2017 | Chapman ............... F16C 1/10 |
| 2007/0149951 | A1 | * | 6/2007 | Wu .................... A61M 25/09 604/526 |
| 2007/0297778 | A1 | * | 12/2007 | Lange ............... G03B 37/005 396/19 |
| 2009/0038093 | A1 | * | 2/2009 | Irwin ................ B08B 9/0436 15/104.095 |
| 2009/0083915 | A1 | * | 4/2009 | Cicchelli .............. B08B 9/045 15/3 |
| 2010/0100055 | A1 | * | 4/2010 | Mustapha .............. A61F 2/95 604/246 |
| 2010/0208055 | A1 | * | 8/2010 | Olsson ................. H01B 7/182 348/84 |
| 2010/0208056 | A1 | * | 8/2010 | Olsson ................. H04N 7/185 348/84 |
| 2012/0110761 | A1 | | 5/2012 | Ripperger et al. |
| 2012/0300057 | A1 | * | 11/2012 | Bartucciotto .......... B08B 9/045 348/84 |
| 2014/0192180 | A1 | * | 7/2014 | Sooy ................. E21B 47/0002 348/85 |
| 2016/0139061 | A1 | * | 5/2016 | Kesselberg ........... G03B 15/03 348/37 |
| 2016/0305891 | A1 | * | 10/2016 | Olsson ................ G01N 21/954 |

OTHER PUBLICATIONS

Katy Spring & MFG. Inc., "Nested Compression Springs," Blog, Jun. 25, 2012, Texas http://www.katyspring.com/blog/2012/06/25/nested-compression-springs-katy-spring/.

* cited by examiner

SPRING ASSEMBLIES WITH VARIABLE FLEXIBILITY FOR USE WITH PUSH-CABLES AND PIPE INSPECTION SYSTEMS

CROSS-REFERENCE TO RELATED APPLICATIONS

This application is a continuation of and claims priority to U.S. Utility patent application Ser. No. 15/296,018, entitled SPRING ASSEMBLIES WITH VARIABLE FLEXIBILITY FOR USE WITH PUSH-CABLES AND PIPE INSPECTION SYSTEMS, filed Oct. 17, 2016, which is a continuation of and claims priority to U.S. Utility patent application Ser. No. 14/271,255, now U.S. Pat. No. 9,477,147, entitled SPRING ASSEMBLIES WITH VARIABLE FLEXIBILITY FOR USE WITH PUSH-CABLES AND PIPE INSPECTION SYSTEMS, filed May 6, 2014, which claims priority under 35 U.S.C. § 119(e) to U.S. Provisional Patent Application Ser. No. 61/820,640, filed on May 7, 2013, entitled SPRING ASSEMBLIES WITH IMPROVED FLEXIBILITY FOR USE WITH PUSH-CABLES AND PIPE INSPECTION SYSTEMS, and to U.S. Provisional Patent Application Ser. No. 61/984,029, filed on Apr. 24, 2014, entitled SPRING ASSEMBLIES WITH VARIABLE FLEXIBILITY FOR USE WITH PUSH-CABLES AND PIPE INSPECTION SYSTEMS. The content of each of these applications is incorporated by reference herein in its entirety for all purposes.

FIELD

This disclosure relates generally to push-cables and systems using push-cables. More specifically, but not exclusively, this disclosure relates to push-cables including a spring assembly for use in video pipe inspection systems.

BACKGROUND

Push-cables for deploying cameras or other pipe inspection or cleaning devices into pipes or cavities are known in the art. While a largely rigid push-cable may be effective for deploying a push-cable into a pipe or other conduit having relatively direct and unobstructed cavities, the rigidity of such a push-cable can make maneuvering around turns or other obstacles within pipes or conduits having curves, bends, or obstructions difficult.

Typical existing push-cables utilize a spring assembly having a single coil spring with uniform flexibility. The spring is typically positioned between the push-cable and camera or other pipe inspection or pipe cleaning device. While these single spring assemblies may provide some aid in preventing the push-cable from snagging around turns or other obstacles within the pipe or conduit, these devices are frequently inadequate in avoiding becoming blocked or stuck within pipes that are being inspected or cleaned.

Accordingly, there is a need in the art to address the above-described as well as other problems.

SUMMARY

This disclosure relates generally to push-cables and systems using push-cables. More specifically, but not exclusively, this disclosure relates to push-cables that include a spring assembly having varying flexibility for use in video pipe inspection systems or other systems where push-cables are used.

For example, in one aspect, the disclosure relates to a push-cable system. The push-cable system may include, for example, a push-cable having a proximal end and a distal end, with a spring assembly having varying flexibility coupled to or near the distal end. The spring assembly may include an outer coiled spring having a proximal and a distal end, and an inner coiled spring nested at least partially within the outer coiled spring.

In another aspect, the disclosure relates to a spring assembly having varying flexibility. The spring assembly may be coupled to a camera head and/or other assembly such as a jetting or cleaning tool and/or a push-cable, such as in a video inspection system. The spring assembly may, for example, include an outer coiled spring having a proximal and a distal end and an inner coiled spring nested at least partially within the outer coiled spring.

In another aspect, the disclosure relates to a spring assembly which may include an outer spring and one or more nested inner springs of varied length arranged such that a front section or sections of the spring assembly may be more flexible than a rear section or sections. A nested inner spring may be shorter than an outer spring, and the nested inner spring may be positioned only within a rear section of the outer spring. The front section of the outer spring may be easier to bend and flex than the rear section containing both the outer spring and nested inner spring. In some embodiments the outer spring may be shorter than an inner spring or springs.

In another aspect, the disclosure relates to a spring for use in a push-cable spring assembly. The spring may include, for example, a wire or ribbon wound into a coiled spring. The coiled spring may include a first lengthwise section and a second lengthwise section. The first lengthwise section may have a first cross-sectional coil area, and the second lengthwise section may have a second cross-sectional coil area that is different from the first cross-sectional area. One section of the spring may, for example, have a plurality of closed coils. A second section of the spring may have a plurality of open coils. A plurality of coils in the first lengthwise section may be closed coils. A plurality of coils in the second section may be open coils.

In another aspect, a nested inner spring may connect to a safety cable which in turn may directly or indirectly connect to a pipe inspection device, such as a camera. Such a nested inner spring with connected safety cable may function as a fail-safe for securing the camera or other pipe inspection device. The nested inner spring may function, in part, as a component of the fail-safe assembly in securing directly or indirectly to the safety cable and push-cable.

Various additional aspects, features, and functionality are further described below in conjunction with the appended Drawings.

BRIEF DESCRIPTION OF THE DRAWINGS

The present application may be more fully appreciated in connection with the following detailed description taken in conjunction with the accompanying drawings, wherein.

DETAILED DESCRIPTION OF EMBODIMENTS

Overview

Figure 1:
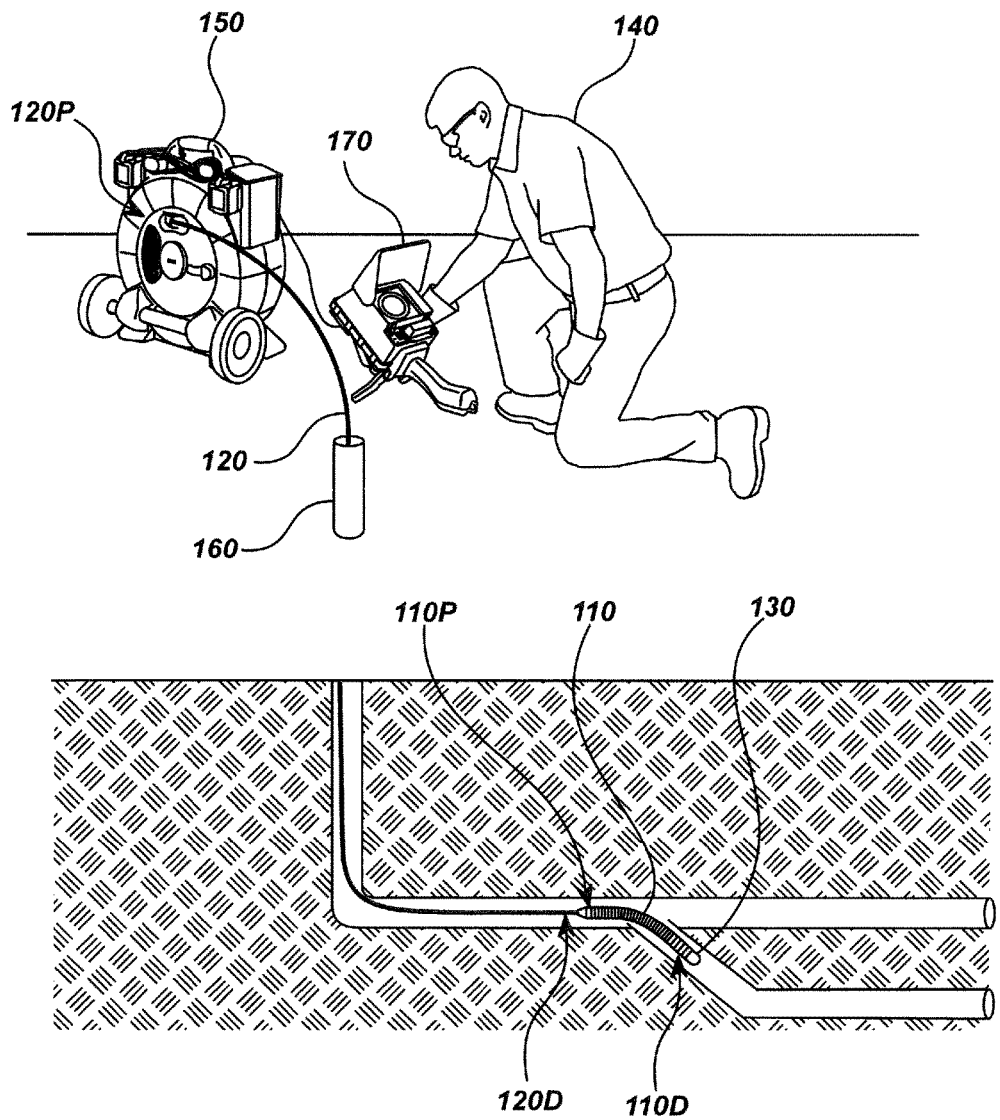
FIG. 1 is an illustration of a user deploying a push-cable with a nested spring assembly embodiment into a pipe.

This disclosure relates generally to push-cables and systems using push-cables. More specifically, but not exclusively, this disclosure relates to push-cables including a spring assembly for use in video pipe inspection systems.

For example, in one aspect, a spring assembly in accordance with aspects of the present disclosure may include an outer spring and one or more nested inner springs of varied length arranged such that a front section or sections of the spring assembly are more flexible than a rear section or sections. In one embodiment, a nested inner spring may be shorter than an outer spring, with the nested inner spring positioned only in a rear section within the outer spring. The front section of the outer spring may thereby be easier to bend and flex than the rear section which includes both the outer spring and the nested inner spring. In alternative embodiments, the outer spring may be shorter than an inner spring or springs.

In another aspect, a nested inner spring may connect to a safety cable which in turn may connect to a pipe inspection device or assembly, such as a camera or other imaging or sensing device. In some embodiments, the pipe inspection device may also include pipe cleaning apparatus such as high pressure jetter heads or cutting tools to clear pipe or cavity obstructions. Such a nested inner spring with connected safety cable may function as a fail-safe for securing the camera or other pipe inspection device or assembly. The nested inner spring may function, in part, as a component of this fail-safe assembly in securing directly or indirectly to the safety cable and push-cable. In alternate embodiments, a safety cable may directly or indirectly secure a camera or other pipe inspection device or assembly to the push-cable.

In another aspect, the ease by which sections of each spring may bend or flex may be altered by increasing the gap distance between various windings of coils in various sections, either continuously or discretely. In alternate embodiments, various other mechanisms of varying the ease/difficulty by which each spring and/or sections of each spring bend or flex may include, but are not limited to, varying materials used or material properties across spring elements or within spring elements, varying thickness or cross-section and/or shape of materials used to form springs, varying the diameter of windings on either the outer spring and/or nested inner spring or springs, and/or combinations thereof.

In another aspect, a pipe inspection system embodiment may include a cable-reel drum for storing and deploying a push-cable, a spring assembly, a camera head such as a self-leveling or other camera head, a pipe sonde, utility locators, and/or camera control units (CCUs). In alternate pipe inspection system embodiments, various other pipe inspection devices, assemblies, and apparatuses may be used with the nested spring assembly embodiments of the present disclosure including, but not limited to, devices, assemblies, and apparatuses as described in the various patents and patent applications incorporated by reference herein.

Camera heads typically include imaging elements, processing elements, memory, and other electronics that generate heat and may also be heat sensitive. In another aspect, a pipe inspection system in accordance with various aspects may include a camera head guide that may couple tightly to a camera head housing and include thermally conductive materials such as aluminum, copper, stainless steel, thermally conductive plastics, composite materials, ceramics, and the like in order to aid in drawing heat away from heat generating elements and heat sensitive components within the camera head. Such a camera head guide may further be configured to aid in centering a camera head within the pipe or conduit, guiding it through obstructions, and protecting it from damage. In alternative embodiments, various other camera head guides or pipe guides may be used, such as those described in patents and applications incorporated herein such as, for example, co-assigned U.S. Pat. No. 8,540,429, entitled SNAP-ON PIPE GUIDE, which is incorporated by reference herein.

In another aspect, the disclosure relates to a push-cable system. The push-cable system may include, for example, a push-cable having a proximal end and a distal end, and a spring assembly coupled to the distal end. The spring assembly may have variable flexibility and may include an outer coiled spring having a proximal and a distal end, and an inner coiled spring nested at least partially within the outer coiled spring.

The system may further include, for example, a push-cable connector element. The push-cable connector element may be coupled to the proximal end of the outer coiled spring to couple the push-cable to the spring assembly. The push-cable connector element may include an outer spring threads feature for coupling to a spring or springs. The outer spring threads feature may have a threaded element shaped to mate with a corresponding coil threading of the outer coiled spring. The push-cable connector element may include an inner spring threads feature for coupling to a spring or springs. The inner spring threads feature may have a threaded element shaped to mate with a corresponding coil threading of the inner coiled spring.

The system may further include, for example, an inner spring mounting element disposed within the outer coil spring. The inner spring mounting element may include a threaded element. The threaded element may be shaped to mate with a corresponding coil threading of the inner coiled spring.

The coils of the inner coiled spring may, for example, be wound in a direction opposite that of the coils of the outer coiled spring. The coils of the inner coiled spring may alternately be wound in a direction the same as that of the outer coiled spring.

One or both of the inner and outer coil springs may, for example, include a first section having two or more successive coils substantially in contact with each other, and may include a second section having a gap between two or more successive coils. One or both of the inner and outer coil springs may include a section having gaps between successive coils that increase in length. One or both of the inner and outer coil springs may include a first section having a first gap between two or more successive coils, and may have a second section having a second gap different from the first gap, between two or more successive coils. One or both of the inner and outer coils may include a first section of a first material, and a second section of a second material different from the first material.

One or both of the inner and outer coils may, for example, include a first section having one or more coils of a first coil diameter, and a second section of one or more coils having a second coil diameter different from the first coil diameter. One or both of the inner and outer coils may include a section having successively increasing coil diameters. One or both of the inner and outer coils may include a first section having one or more coils of a first cross-sectional area, and a second section having one or more coils of a second cross-sectional area different from the first cross-sectional area. One or both of the inner and outer coils may include a section having successively increasing coil cross-sectional areas. One or both of the inner and outer coils may include a section having successively varying coil cross-sectional shapes. One or both of the inner and outer coils may include a first section having two or more coils of a first pitch, and a second section of two or more coils of a second pitch different from the first pitch. One or both of the inner and outer coils may include a section having successively varying coil pitches.

The inner spring may, for example, be shorter than the outer spring. The inner spring may be nested within the outer spring at the proximal end of the outer spring. The inner spring may be nested entirely within the outer spring. The inner spring may be shorter in length than the outer spring, and the inner spring may be positioned at the proximal end of the outer spring. The inner spring may have a length of less than approximately half the length of the outer spring. One or both of the inner and outer springs may include three or more sections. Each of the three or more sections may have different flexibility and/or bending characteristics.

The system may, for example, further include one or more connecting wires. The one or more connecting wires may be disposed at least partially within the spring assembly. The connecting wires may include one or more signal wires, such as wires for carrying control signals, image or video signals, and/or other data or information signals through the push-cable and spring assembly. The connecting wires may include electrical signal wires. The connecting wires may include electrical power wires. The connecting wires may include waveguides. The connecting wires may include optical fibers.

The system may, for example, further include a transmitter or transceiver element disposed within the outer coiled spring. The system may further include a disconnect element for uncoupling the transmitter element from the push-cable system. The transmitter element may be a sonde. The sonde may generate magnetic field signals for sensing by a corresponding buried object locator device. The sonde may be powered using batteries and/or may be powered via power provided from one of the connecting wires.

The system may, for example, further include a safety cable, which may be disposed within the outer coiled spring. The safety cable may be coupled to the push-cable and/or camera head and/or spring assembly to prevent damage to the system in the event of overextension or breakage. The system may further include a camera head. The camera head may be coupled to the distal end of the push-cable assembly. The camera head may include one or more imaging elements, one or more lenses or optical elements, one or more processing elements, one or more memories, one or more electronics elements, one or more wired or wireless communication elements such as a transmitter, a receiver, a transceiver, and/or other elements such as, for example, are described in the applications incorporated by reference herein. The camera head may include or be coupled to or integral with a sonde. The camera head may further include one or more lighting elements. The one or more lighting elements may be LEDs or other lighting elements. The lighting elements may be visible lighting elements and/or may be infrared or ultraviolet lighting elements. The lighting elements may be an array of LEDs or other lighting elements. The one or more lighting elements may be powered via the connecting wires. The camera head may include a camera spring threads feature for coupling to one or more springs. The camera springs threads feature may have a threaded element. The threaded element may be shaped to mate with a corresponding coil threading of the inner and/or outer coiled spring. The system may further include a camera guide coupled to the camera head.

The outer coiled spring assembly may, for example, include a plurality of outer spring elements. One of the plurality of outer spring elements may be substantially the same, or one or more of the plurality of outer spring elements may be configured with different flex and/or bend characteristics than others of the plurality of outer spring elements.

One or more of the plurality of outer spring elements may, for example, include a first section having two or more successive coils substantially in contact with each other, and a second section may have a gap between two or more successive coils. One or more of the plurality of outer spring elements may include a first section of a first material, and a second section of a second material. One or more of the plurality of outer spring elements may include a section having successively increasing coil diameters. One or more of the plurality of outer spring elements may include a first section having one or more coils of a first cross-sectional area, and a second section having one or more coils of a second cross-sectional area different from the first cross-sectional area. One or more of the plurality of outer spring coils may include a section having successively increasing coil cross-sectional areas. One or more of the plurality of outer spring coils may include a section having successively varying coil cross-sectional shapes. One or more of the plurality of outer spring coils may include a section having two or more coils of a first pitch, and a second section of two or more coils of a second pitch different from the first pitch. One or more of the plurality of outer spring coils may include a section having successively varying coil pitches.

The inner coiled spring may, for example, include a first section having two or more successive coils substantially in contact with each other, and a second section having a gap between two or more successive coils. The inner coiled spring may include a first section of a first material and a second section of a second material. The inner coiled spring may include a section having successively increasing coil diameters. The inner coiled spring may include a first section having one or more coils of a first cross-sectional area, and a second section having one or more coils of a second cross-sectional area different from the first cross-sectional area. The inner coiled spring may include a section having successively increasing coil cross-sectional areas. The inner coiled spring may include a section having successively varying coil cross-sectional shapes. The inner coiled spring may include a section having two or more coils of a first pitch, and a second section of two or more coils having a second pitch different from the first pitch. The inner coiled spring may include a section having successively varying coil pitches.

The coils of the inner coiled spring may, for example, be wound in the same direction as the coils of one or more of the outer coiled spring elements. Alternately, the coils of the inner coil spring may be wound in a different direction than the coils of one or more of the outer coil spring elements.

The outer coiled spring may, for example, include a first section having a first plurality of coils having a first coil diameter and a second, reduced diameter section having a second plurality of coils with diameters less than the diameter of the first plurality of coils. The reduced diameter section may have a length less than approximately 10 percent of the outer coiled spring length. The inner coiled spring may have tapered ends such that coils of one or both of the end windings of the inner coiled spring have diameters greater than the diameter of coils central to the inner coiled spring. The system may further include one or more connecting wires disposed within the outer coiled spring.

The system may, for example, further include a cable reel for storing the push-cable. The system may further include a camera control unit (CCU). The CCU may be coupled to or integral with the cable reel or may be separate from the cable reel.

In another aspect, the disclosure relates to a spring assembly having variable flexibility. The spring assembly may be coupled to a camera head and/or a push-cable, such as in a video inspection system. The spring assembly may, for example, include an outer coiled spring having a proximal and a distal end and an inner coiled spring nested at least partially within the outer coiled spring.

The spring assembly may further include, for example, a push-cable connector element. The push-cable connector element may be coupled to the proximal end of the outer coiled spring to couple the push-cable to the spring assembly. The push-cable connector element may include an outer spring threads feature for coupling to a spring. The outer spring threads feature may have a threaded element shaped to mate with a corresponding coil threading of the outer coiled spring. The push-cable connector element may include an inner spring threads feature for coupling to a spring. The inner spring threads feature may have a threaded element shaped to mate with a corresponding coil threading of the inner coiled spring.

The spring assembly may further include, for example, an inner spring mounting element disposed within the outer coil spring. The inner spring mounting element may include a threaded element. The threaded element may be shaped to mate with a corresponding coil threading of the inner coiled spring.

The coils of the inner coiled spring may, for example, be wound in a direction opposite that of the coils of the outer coiled spring. The coils of the inner coiled spring may alternately be wound in a direction the same as that of the outer coiled spring.

One or both of the inner and outer coil springs may, for example, include a first section having two or more successive coils substantially in contact with each other, and may include a second section having a gap between two or more successive coils. One or both of the inner and outer coil springs may include a section having gaps between successive coils that increase in length. One or both of the inner and outer coil springs may include a first section having a first gap between two or more successive coils, and may have a second section having a second gap different from the first gap, between two or more successive coils. One or both of the inner and outer coils may include a first section of a first material, and a second section of a second material different from the first material. One or both of the inner and outer coils may include a first section having one or more coils of a first coil diameter, and a second section of one or more coils having a second coil diameter different from the first coil diameter.

One or both of the inner and outer coils may, for example, include a section having successively increasing coil diameters. One or both of the inner and outer coils may include a first section having one or more coils of a first cross-sectional area, and a second section having one or more coils of a second cross-sectional area different from the first cross-sectional area. One or both of the inner and outer coils may include a section having successively increasing coil cross-sectional areas. One or both of the inner and outer coils may include a section having successively varying coil cross-sectional shapes. One or both of the inner and outer coils may include a first section having two or more coils of a first pitch, and a second section of two or more coils of a second pitch different from the first pitch. One or both of the inner and outer coils may include a section having successively varying coil pitches.

The inner spring may, for example, be shorter than the outer spring. The inner spring may be nested within the outer spring at the proximal end of the outer spring. The inner spring may be nested entirely within the outer spring. The inner spring may be shorter in length than the outer spring, and the inner spring may be positioned at the proximal end of the outer spring. The inner spring may have a length of less than approximately half the length of the outer spring. One or both of the inner and outer springs may include three or more sections. Each of the three or more sections may have different flexibility or bending characteristics.

The spring assembly may, for example, further include one or more connecting wires. The one or more connecting wires may be disposed at least partially within the spring assembly. The connecting wires may include one or more signal wires, such as wires for carrying control signals, image or video signals, and/or other data or information signals through the push-cable and spring assembly. The connecting wires may include electrical power wires. The connecting wires may include waveguides. The connecting wires may include electrical signal wires. The connecting wires may include optical fibers.

The spring assembly may, for example, further include a transmitter element disposed within the outer coiled spring. The spring assembly may further include a disconnect element for uncoupling the transmitter element from the push-cable system. The transmitter element may be a sonde. The sonde may generate magnetic field signals for sensing by a corresponding buried object locator device. The sonde may be powered using batteries and/or may be powered via power provided from one of the connecting wires.

The spring assembly may, for example, further include a safety cable disposed within the outer coiled spring. The safety cable may be coupled to the push-cable and/or camera head and/or spring assembly to prevent damage to the system in the event of overextension or breakage.

The outer coiled spring assembly may, for example, include a plurality of outer spring elements. One of the plurality of outer spring elements may be substantially the same or one or more of the plurality of outer spring elements may be configured with different flex and/or bend characteristics than others of the plurality of outer spring elements.

One or more of the plurality of outer spring elements may, for example, include a first section having two or more successive coils substantially in contact with each other, and a second section having a gap between two or more successive coils. One or more of the plurality of outer spring elements may include a first section of a first material, and a second section of a second material. One or more of the plurality of outer spring elements may include a section having successively increasing coil diameters. One or more of the plurality of outer spring elements may include a first section having one or more coils of a first cross-sectional area, and a second section having one or more coils of a second cross-sectional area different from the first cross-sectional area. One or more of the plurality of outer spring coils may include a section having successively increasing coil cross-sectional areas. One or more of the plurality of outer spring coils may include a section having successively varying coil cross-sectional shapes. One or more of the plurality of outer spring coils may include a section having two or more coils of a first pitch, and a second section of two or more coils of a second pitch different from the first pitch. One or more of the plurality of outer spring coils may include a section having successively varying coil pitches.

The inner coiled spring may, for example, include a first section having two or more successive coils substantially in contact with each other, and a second section having a gap between two or more successive coils. The inner coiled spring may include a first section of a first material, and a second section of a second material. The inner coiled spring may include a section having successively increasing coil diameters. The inner coiled spring may include a first section having one or more coils of a first cross-sectional area, and a second section having one or more coils of a second cross-sectional area different from the first cross-sectional area. The inner coiled spring may include a section having successively increasing coil cross-sectional areas. The inner coiled spring may include a section having successively varying coil cross-sectional shapes. The inner coiled spring may include a section having two or more coils of a first pitch, and a second section of two or more coils having a second pitch different from the first pitch. The inner coiled spring may include a section having successively varying coil pitches.

The coils of the inner coil spring may, for example, be wound in the same direction as the coils of one or more of the outer coil spring elements. Alternately, the coils of the inner coil spring may be wound in a different direction than the coils of one or more of the outer coil spring elements.

The outer coiled spring may, for example, include a first section having a first plurality of coils having a first coil diameter, and a second, reduced diameter section having a second plurality of coils with diameters less than the diameter of the first plurality of coils. The reduced diameter section may have a length less than approximately 10 percent of the outer coiled spring length. The inner coiled spring may have tapered ends such that coils of one or both of the end windings of the inner coiled spring have diameters greater than the diameter of coils central to the inner coiled spring. The spring assembly may further include one or more connecting wires disposed within the outer coiled spring.

In another aspect, the disclosure relates to a spring for use in a push-cable spring assembly. The spring may include, for example, a wire or ribbon wound into a coiled spring. The coiled spring may include a first lengthwise section and a second lengthwise section. The first lengthwise section may have a first cross-sectional coil area, and the second lengthwise section may have a second cross-sectional coil area that is different from the first cross-sectional area. The spring may be wound from a wire into the coil. The coils of the first lengthwise section may have a different cross-sectional coil shape than the coils of the second cross-sectional section. The second lengthwise section may have a varying cross-sectional coil shape. The second lengthwise section may have a decreasing coil area towards a distal end of the coiled spring. The varying cross-sectional shape may be formed by a boring or drilling operation. The boring or drilling operation may be done to a coiled spring initially having coils of substantially the same cross-sectional shape and/or area.

Various additional aspects, features, and functions are described below in conjunction with FIG. 1 through FIG. 20 of the appended Drawings. The various aspects described above as well as subsequently herein may be added to or combined with each other to provide additional embodiments of flexible push-cables and push-cable systems.

It is noted that as used herein, the term, "exemplary" means "serving as an example, instance, or illustration." Any aspect, detail, function, implementation, and/or embodiment described herein as "exemplary" is not necessarily to be construed as preferred or advantageous over other aspects and/or embodiments.

The following exemplary embodiments are provided for the purpose of illustrating examples of various aspects, details, and functions of the present disclosure. However, the described embodiments are not intended to be in any way limiting. It will be apparent to one of ordinary skill in the art that various aspects may be implemented in other embodiments within the spirit and scope of the present disclosure.

Example Spring Assembly Embodiments and Systems

This disclosure relates generally to push-cables and systems using push-cables, such as pipe inspection or cleaning systems, as well as buried utility locating systems that use signals generated from devices coupled to push-cables such as sondes or cameras.

Details of push-cable, pipe inspection, sonde, camera, and buried utility locating systems that may be combined with the teachings and disclosures herein in various embodiments are described in co-assigned United States patent applications and patents including, for example, U.S. patent application Ser. No. 14/033,349, filed Sep. 20, 2013, entitled PIPE INSPECTION SYSTEM WITH SNAP-ON PIPE GUIDES; U.S. patent application Ser. No. 13/941,381, filed Jul. 13, 2013, entitled SELF-GROUNDING TRANSMITTING PORTABLE CAMERA CONTROLLER FOR USE WITH PIPE INSPECTION SYSTEM; U.S. patent application Ser. No. 13/787,711, entitled DUAL SENSED LOCATING SYSTEMS & METHODS, filed Mar. 6, 2013; U.S. patent application Ser. No. 13/774,351, filed Feb. 22, 2013, entitled DOCKABLE TRIPODAL CAMERA CONTROL UNIT; U.S. patent application Ser. No. 13/754,767, filed Jan. 30, 2013, entitled ADJUSTABLE VARIABLE RESOLUTION INSPECTION SYSTEMS AND METHODS; U.S. patent application Ser. No. 13/676,018, filed Nov. 13, 2012, entitled PORTABLE PIPE INSPECTION SYSTEMS AND APPARATUS; U.S. patent application Ser. No. 13/589,948, filed Aug. 20, 2012, entitled LIGHT WEIGHT SEWER CABLE; U.S. patent application Ser. No. 13/346,668, filed Jan. 9, 2012, entitled PORTABLE CAMERA CONTROLLER PLATFORM FOR USE WITH PIPE INSPECTION SYSTEMS; U.S. patent application Ser. No. 13/214,208, filed Aug. 21, 2011, entitled ASYMMETRIC DRAG FORCE BEARINGS FOR USE WITH PUSH-CABLE STORAGE DRUMS; U.S. patent application Ser. No. 13/073,919, filed Mar. 28, 2011, entitled PIPE INSPECTION SYSTEM WITH JETTER PUSH-CABLE; U.S. patent application Ser. No. 12/939,591, filed Nov. 4, 2010, entitled SMART PERSONAL COMMUNICATION DEVICES AS USER INTERFACES; U.S. patent application Ser. No. 12/704,808, filed Feb. 12, 2010, entitled PIPE INSPECTION SYSTEM WITH REPLACEABLE CABLE STORAGE DRUM; U.S. patent application Ser. No. 11/679,092, filed Feb. 26, 2007, entitled LIGHT WEIGHT SEWER CABLE; U.S. Provisional Patent Application Ser. No. 61/174,429, filed Apr. 30, 2009, entitled LOG FILE FOR CAMERA INSPECTION SYSTEMS; U.S. Pat. No. 8,540,429, entitled SNAP-ON PIPE GUIDE, issued Sep. 24, 2013; U.S. Pat. No. 8,395,661, entitled PIPE INSPECTION SYSTEM WITH SELECTIVE IMAGE CAPTURE, issued Mar. 12, 2013; U.S. Pat. No. 8,289,385, entitled PUSH-CABLES FOR PIPE INSPECTION SYSTEM, issued Oct. 16, 2012; U.S. Pat. No. 6,958,767, entitled VIDEO PIPE INSPECTION SYSTEM EMPLOYING NON-ROTATING CABLE STORAGE DRUM, issued Oct. 25, 2005; U.S. Pat. No. 6,908,310, entitled SLIP RING ASSEMBLY WITH INTEGRAL POSITION ENCODER, issued Jun. 21, 2005; U.S. Pat. No. 6,862,945, entitled CAMERA GUIDE FOR VIDEO PIPE INSPECTION SYSTEM, issued Mar. 8, 2005; U.S. Pat. No. 6,831,679, entitled VIDEO CAMERA HEAD WITH THERMAL FEEDBACK LIGHTING CONTROL, issued Dec. 14, 2004; U.S. Pat. No. 6,545,704, entitled VIDEO PIPE INSPECTION DISTANCE MEASURING SYSTEM, issued Apr. 8, 2003; U.S. Pat. No. 5,939,679, entitled VIDEO PUSH-CABLE, issued Aug. 17, 1999; U.S. Pat. No. 5,808,239, entitled VIDEO PUSH-CABLE, issued Sep. 15, 1998; and U.S. Pat. No. 5,457,288, entitled DUAL PUSH-CABLE FOR PIPE INSPECTION, issued Oct. 10, 1995. The content of each of these patents, publications and applications is incorporated by reference herein in its entirety. The above patents and applications may be collectively referred to herein as the "incorporated applications."

In addition to the specific embodiments described herein, various other embodiments within the scope of the present invention may be implemented by combining the teachings and disclosures herein with those of the above-referenced incorporated applications in various combinations.

Turning to FIG. 1, details of a pipe inspection system embodiment being used in an example inspection operation in accordance with aspects of the present disclosure are illustrated. The pipe inspection system may include a push-cable system including a nested spring assembly 110 secured about a distal or far end 120D of a push-cable 120, which may be connected to a camera head 130 and/or other apparatus (not shown), such as jetter tools, lighting elements (e.g., LEDs, etc.), cutter heads, sondes, transceivers, sensors, and the like, any of which may be pushed into a pipe or cavity for inspection or cleaning operations. A proximal or near end 120P of the push-cable may be physically and/or communicatively coupled to a cable reel 150. The push-cable 120 may be wound on the cable reel 150 for storage or fully or partially unwound and deployed for use (such as shown in FIG. 1).

The camera head 130 may be mechanically and electrically coupled to the push-cable system, such as by being secured to or near a distal end 110D of the nested spring assembly 110, with a proximal end 110P of the nested spring assembly coupled to the push-cable 120 at or near the push-cable's distal end 120D. Other configurations, such as direct coupling of the camera head 130 and push-cable, or including other interstitial elements disposed between the push-cable and camera head or other assembly, may also be used in alternate embodiments.

The push-cable may be any of a variety of push-cables such as, for example, a push-cable as described in the incorporated applications such as co-assigned U.S. patent application Ser. No. 11/679,092, entitled LIGHT WEIGHT SEWER CABLE, filed Feb. 26, 2007, and/or U.S. patent application Ser. No. 12/371,540, entitled PUSH-CABLES FOR PIPE INSPECTION SYSTEM, filed Feb. 13, 2009, and/or U.S. patent application Ser. No. 13/073,919, entitled PIPE INSPECTION SYSTEM WITH JETTER PUSH-CABLE, filed Mar. 28, 2011, and/or U.S. patent application Ser. No. 13/589,948, entitled LIGHT WEIGHT SEWER CABLE, filed Aug. 20, 2012, all of which are incorporated by reference herein.

In use, push-cable 120, along with connected nested spring assembly 110 and camera head 130 (and/or other apparatus/devices such as are described herein), may be deployed by a user 140 from cable reel 150 into a pipe 160 or other cavity. The user 140 may control camera head operation and/or monitor imagery and data (e.g., images, video, sensor data, motion/position data, accelerometer data, compass or other magnetic sensor data, and the like) captured from within the pipe 160 by the camera head as controlled and/or displayed upon a camera control unit (CCU) 170 and/or other electronic computing devices or systems, such as coupled notebook computers, tablets, cellular phones, or other devices or systems. A CCU such as CCU 170 as shown typically includes a visual display element, such as an LCD panel, along with input and output controls, electronics for receiving and processing signals from a camera, data storage such as internal or removable memory devices for storage images, video, and/or other data or information, location/position data (e.g., from a GPS receiver or other location/positioning device), and the like. The CCU may also include wired or wireless data transmitters, receivers, or transceivers, such as Wi-Fi, cellular, or other data transmission devices to send and/or receive data, control signals, and/or other information to or from a coupled computing device or network.

The cable reel may, for example, be a cable storage drum reel as described in the incorporated applications, such as in co-assigned U.S. patent application Ser. No. 13/589,948, entitled LIGHT WEIGHT SEWER CABLE DRUM, filed Aug. 20, 2012, and/or U.S. patent application Ser. No. 13/214,208, entitled ASYMMETRIC DRAG FORCE BEARINGS FOR USE WITH PUSH-CABLE STORAGE DRUMS, filed Aug. 21, 2011, U.S. patent application Ser. No. 12/704,808, entitled PIPE INSPECTION SYSTEM WITH REMOVABLE DRUM, filed Feb. 12, 2010, and/or U.S. patent application Ser. No. 11/679,092, entitled LIGHT WEIGHT SEWER CABLE, filed Feb. 26, 2007, all of which are incorporated by reference herein.

The CCU may, for example, be a CCU as described in the incorporated applications, such as in co-assigned U.S. patent application Ser. No. 13/941,381, entitled SELF-GROUNDING TRANSMITTING PORTABLE CAMERA CONTROLLER FOR USE WITH PIPE INSPECTION SYSTEM, filed Jul. 13, 2013, and/or U.S. patent application Ser. No. 13/774,351, entitled DOCKABLE TRIPODAL CAMERA CONTROL UNIT, filed Feb. 22, 2013, and/or U.S. patent application Ser. No. 13/676,018, entitled PORTABLE PIPE INSPECTION SYSTEMS AND APPARATUS, filed Nov. 13, 2012, and/or U.S. patent application Ser. No. 13/346,668, entitled PORTABLE CAMERA CONTROLLER PLATFORM FOR USE WITH PIPE INSPECTION SYSTEMS, filed Jan. 9, 2012, and/or U.S. patent application Ser. No. 12/939,591, entitled SMART PERSONAL COMMUNICATION DEVICES AS USER INTERFACES, filed Nov. 4, 2010, and/or U.S. Provisional Patent Application Ser. No. 61/174,429, entitled LOG FILE FOR CAMERA INSPECTION SYSTEMS, filed Apr. 30, 2009, all of which are incorporated by reference herein.

The camera head may, for example, be a camera head as described in co-assigned U.S. patent application Ser. No. 14/136,104, entitled ROTATING CONTACT ASSEMBLIES FOR SELF-LEVELING CAMERA HEADS, filed Dec. 20, 2013, and/or U.S. patent application Ser. No. 13/775,066, entitled THERMAL EXTRACTION ARCHITECTURE CAMERA HEADS & INSPECTION SYSTEMS, filed Feb. 22, 2013, and/or U.S. patent application Ser. No. 13/754,767, entitled ADJUSTABLE VARIABLE RESOLUTION INSPECTION SYSTEMS AND METHODS, filed Jan. 30, 2013, and/or U.S. patent application Ser. No. 13/676,018, entitled PORTABLE PIPE INSPECTION SYSTEMS AND APPARATUS, filed Nov. 13, 2012, and/or U.S. patent application Ser. No. 13/358,463, entitled SELF-LEVELING INSPECTION SYSTEMS AND METHODS, filed Jan. 25, 2012, and/or U.S. patent application Ser. No. 13/346,668, entitled PORTABLE CAMERA CONTROLLER PLATFORM FOR USE WITH PIPE INSPECTION SYSTEMS, filed Jan. 9, 2012, and/or U.S. Pat. No. 6,862,945, entitled CAMERA GUIDE FOR PIPE INSPECTION SYSTEM, issued Mar. 8, 2005, and/or U.S. Pat. No. 6,697,102, entitled BORE HOLE CAMERA WITH IMPROVED FORWARD AND SIDE VIEW ILLUMINATION, issued Feb. 24, 2004, and/or U.S. Pat. No. 6,831,679, entitled VIDEO CAMERA HEAD WITH THERMAL FEEDBACK LIGHTING CONTROL, issued Dec. 14, 2004, each of which are incorporated by reference herein.

Figure 2:
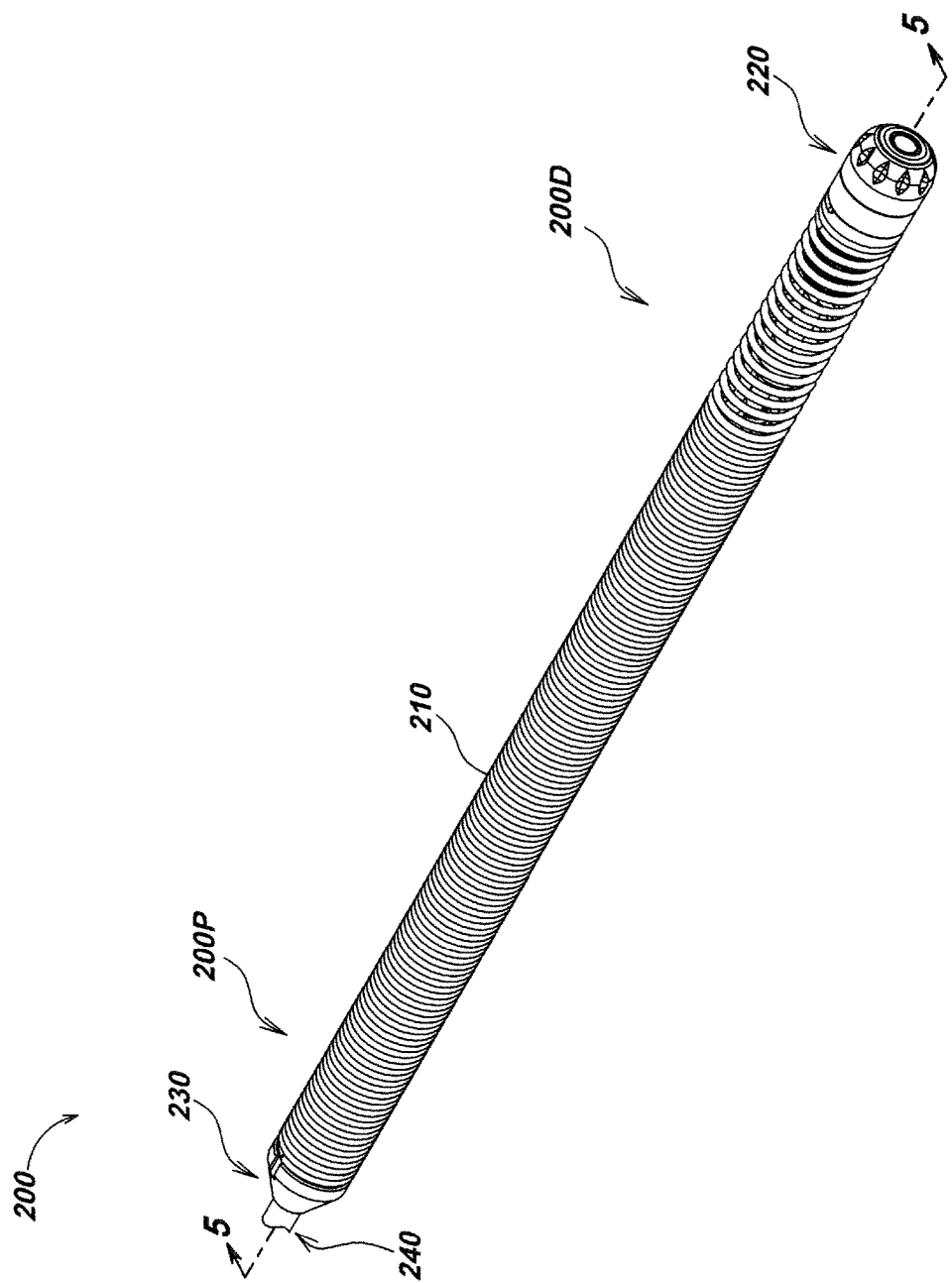
FIG. 2 is an isometric view of a nested spring assembly embodiment with an attached camera head.
Figure 3:
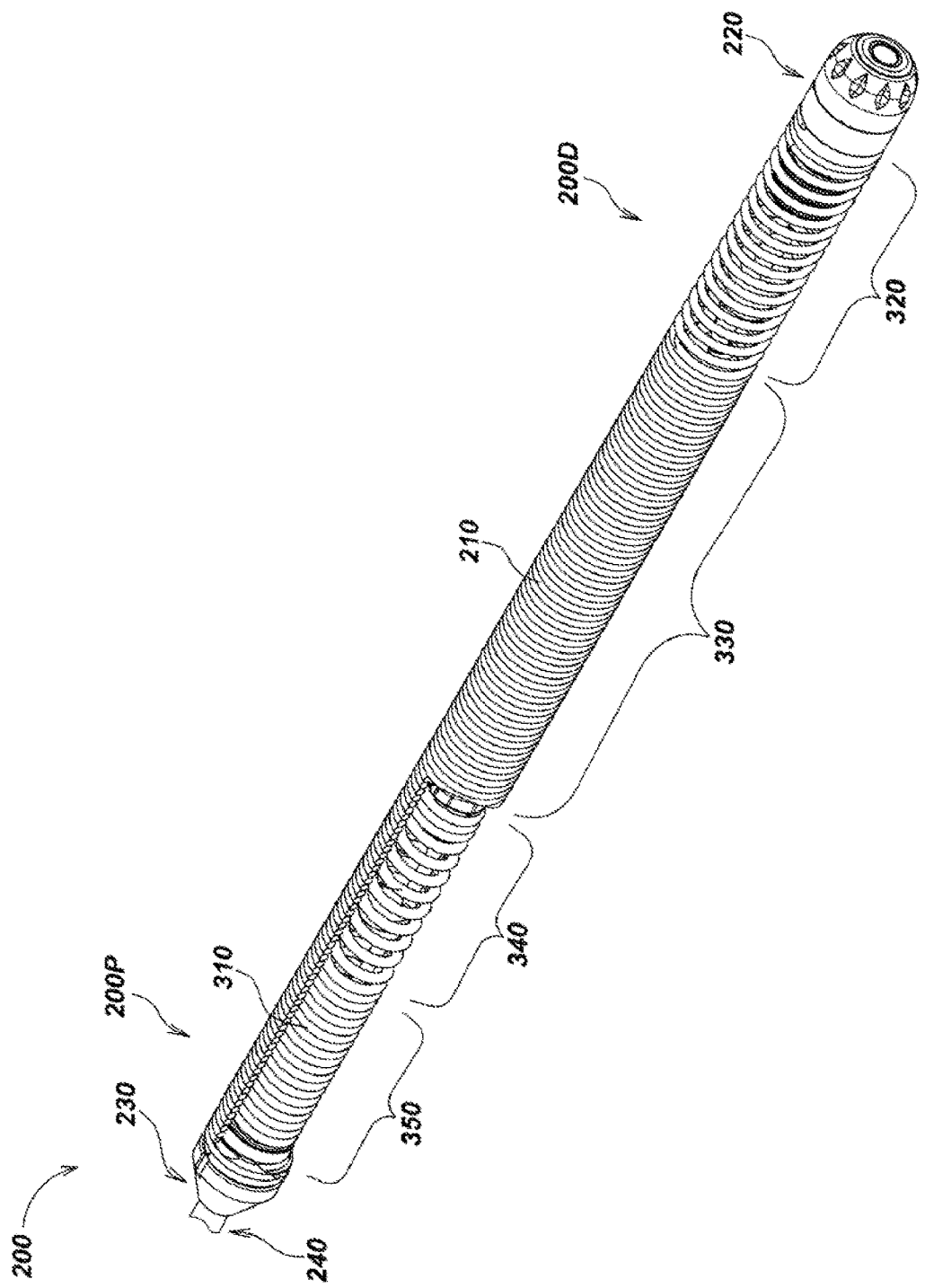
FIG. 3 illustrates the nested spring assembly embodiment of FIG. 2 with a section of the outer spring cut away.

Turning to FIG. 2 and FIG. 3, a variable flexibility nested spring assembly embodiment 200 comprising two springs, in accordance with aspects of the present disclosure, is illustrated. Embodiment 200 may include an outer coiled spring 210, which may enclose or contain at least a portion of a nested inner coiled spring 310 (as shown in cutaway in FIG. 3). A camera head 220 (and/or other elements, such as LED lights, cutting tools or jets for pressure cleaning, etc., not shown) may be secured about the distal or front-most end 200D of the nested spring assembly 200. A push-cable connector element 230 may be coupled to the rear-most or proximal end 200P of the nested spring assembly 200 to secure a push-cable 240 to the nested spring assembly 200.

In some embodiments, the inner and outer springs may be coiled or wound in opposition directions. For example, in nested spring assembly embodiment 200, the winding of coils on the outer spring 210 may be formed so as to be oriented in a direction opposite to the winding direction of coils on the nested inner spring 310 (as seen in FIG. 3). In use, oppositely wound coils may be used to aid in preventing the windings of the outer spring 210 from snagging on windings of the nested inner spring 310. In other embodiments, the winding of coils on each spring may be wound in the same direction.

A section or sections of the coils may have gaps or increased spacing between coil windings on the nested inner spring 310 and/or on the outer spring 210. The gaps may be of similar widths in discrete areas of the coil or coils or may vary across sections of coil or coils in some embodiments. For example, a portion or section of the inner and/or outer coils may have the coils substantially in contact with each other during a released state (i.e., having minimal or no gap), while another portion or section of the coils may have a gap between coils in the released state of a fixed spacing. In some embodiments, the spacing between coils forming the gaps may be the same throughout a section or portion of the coil, whereas, in other embodiments the spacing or gaps may be variable over the length of the coil or a portion of the length of the coil. Coils including variable or discreetly varying pitches may be used in some embodiments. Alternately, or in addition, coils of varying diameters, material properties, coil spacing, and/or combinations of these may be used in various embodiments to vary bend characteristics and/or flexibility across the spring assembly.

In operation, in the embodiment shown in FIG. 3, the distal or front-most gap sections on the nested inner spring 310 and the outer spring 210 may bend and flex with greater ease than the non-gapped sections of each spring due to the spacing between the coils. This may be done to increase the flexibility of the push-cable assembly at or near the camera head and distal end 200D while reducing flexibility at or near the proximal end 200P where the push-cable couples to the nested spring assembly. In various alternative embodiments, various other ways to vary the flexibility by which each spring and/or sections of each spring bends or flexes may include, but are not limited to, varying spring materials used (e.g., by forming springs of different materials, treating sections of the spring differently during manufacturing, and/or using different types of materials within springs, etc.), varying thickness of materials used (e.g., spring coil cross-sections, shapes, and/or diameters), varying the diameter of windings or tapering a section on the springs used, varying the physical properties of the spring across the springs' lengths, varying the pitch, varying the cross-sectional shape, and/or by using other techniques known or developed in the art to vary spring bending and flexing properties and/or combining two or more of the above-described techniques.

Figure 4:
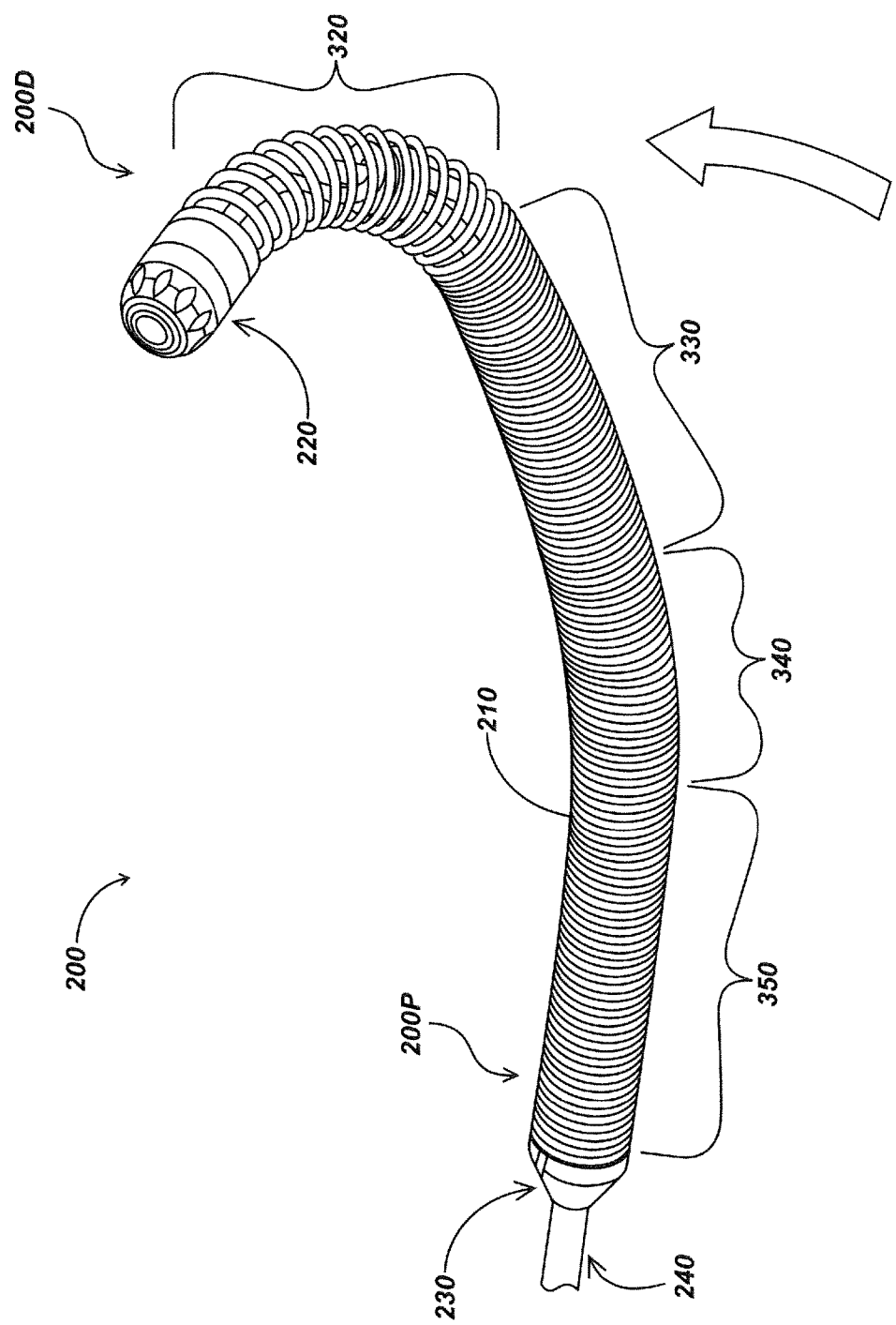
FIG. 4 illustrates the nested spring assembly embodiment of FIG. 2 being forced to bend and flex.

As illustrated in the example embodiments of FIG. 3 and FIG. 4, the nested spring assembly 200 may include two or more sections or portions with different properties so as to bend and flex with a lessening degree of ease the further from the front-most or distal end 200D that the particular section is located. For example, a distal or front-most section 320 of the outer spring may be made to bend and flex with the greatest degree of ease to readily allow camera head movement and ease deployment of the camera head through a pipe or cavity. A front-mid-section 330 may be made to bend and flex but with a lesser degree of ease than the front-most section 320. A rear midsection 340 may be made to bend and flex but with a yet lesser degree of ease than both the front-most section 320 and front mid-section 330. Finally, a proximal or rear-most section 350, near the proximal end 200P of the spring assembly, may be made to bend and flex but with a yet further lessened degree of ease than the front-most section 320, front mid-section 330, and rear midsection 340 to minimize movement between the spring assembly and push-cable.

In some embodiments, the inner spring may be shorter in length than the outer spring, and may have two or more sections with varying properties. For example, as best illustrated in FIG. 3, the distal or front-most section 320 may be comprised primarily of the section of the outer spring 210 with gapped or spaced-apart windings as shown. The front mid-section 330 may be comprised of a section of the outer spring 210 with non-gapped windings (with no corresponding section of the nested inner spring 310 enclosed by this section). The rear mid-section 340 may be comprised of a section of the outer spring 210 with non-gapped windings that also contains a section of the nested inner spring 310 with gapped windings. The rearmost section 350 may be comprised of a section of the outer spring 210 with non-gapped windings that also contains a section of the nested inner spring 310 with non-gapped windings. Various other combinations of inner and outer springs, and/or additional spring layers, having different properties, may be used in alternate embodiments. Spring sectional stiffness may also be controlled by the degree of backwind and/or the degree of coil to coil pretension and/or preload wound into the spring during manufacture.

As illustrated in FIG. 4, the different sections from the rear-most section 350 at the proximal end 200P to the front-most section 320 at the distal end 200D may be made to bend and flex with progressively greater ease (e.g., the spring assembly bends with the greatest ease at the distal end 200D). In alternative embodiments, two or more flexible sections may be created using two or more springs such that different bending characteristics are achieved across the spring assembly.

Figure 5:
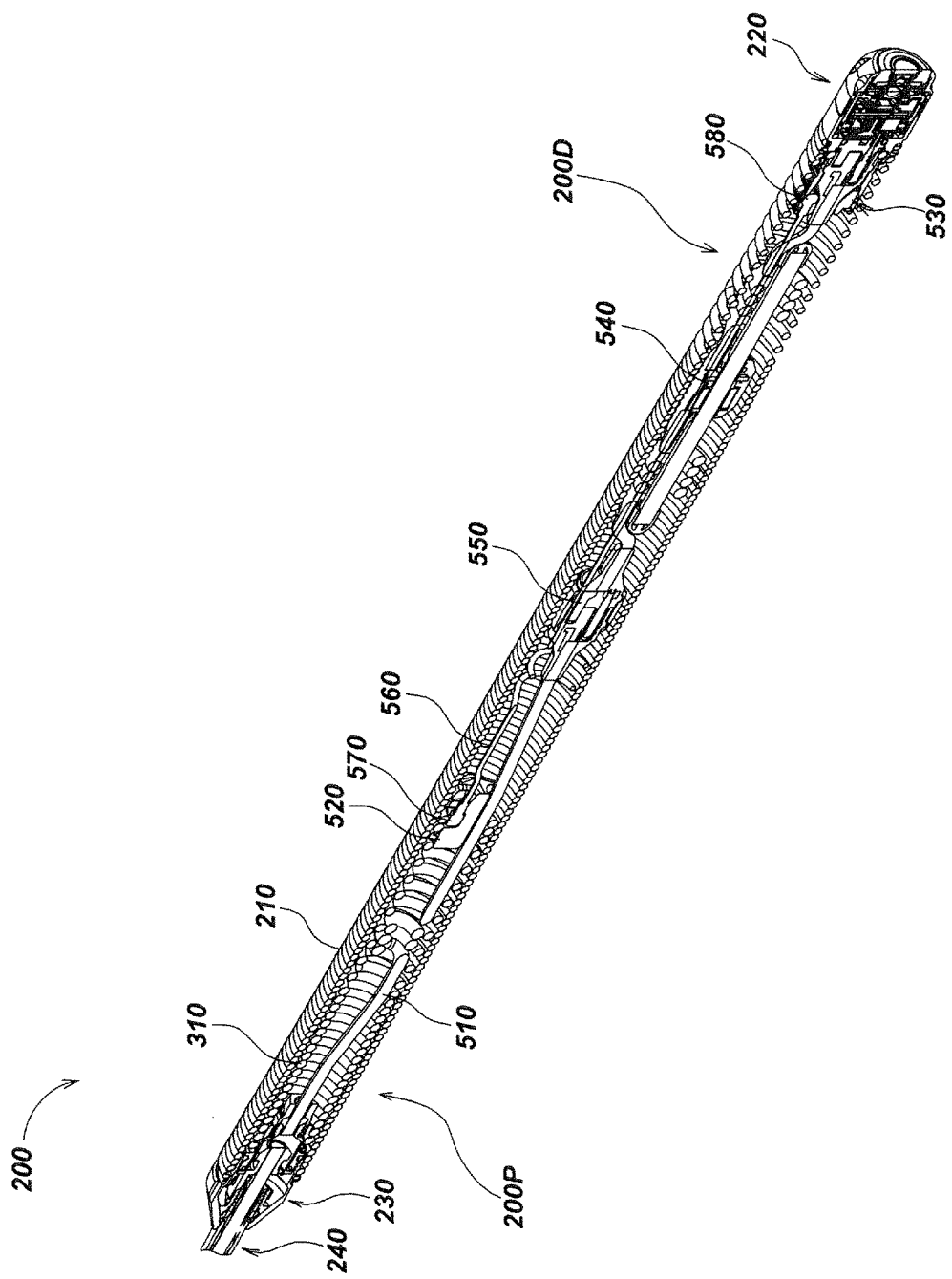
FIG. 5 is a sectional view of the nested spring assembly embodiment of FIG. 2.
Figure 6A:
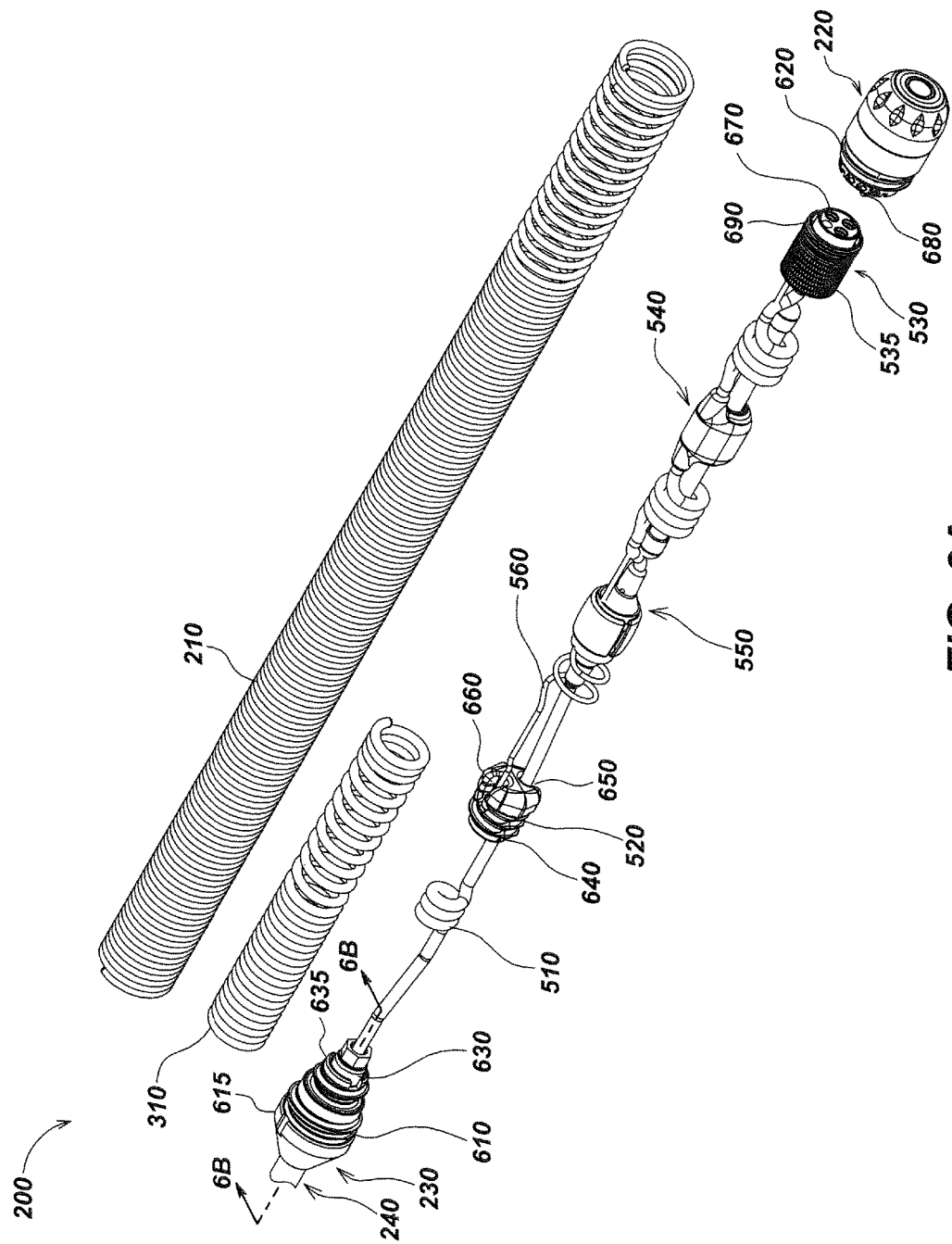
FIG. 6A is a top down partially exploded view of the nested spring assembly embodiment of FIG. 2.
Figure 6B:
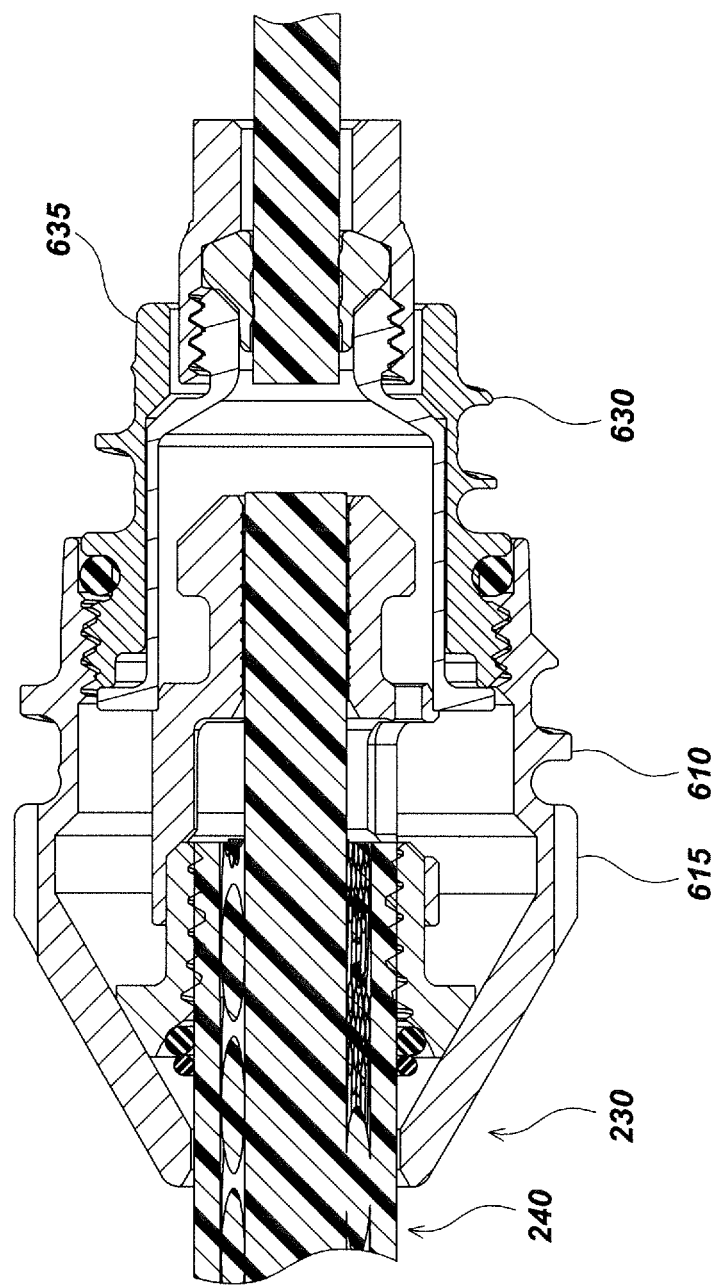
FIG. 6B is a sectional view of a push-cable connector embodiment.
Figure 6C:
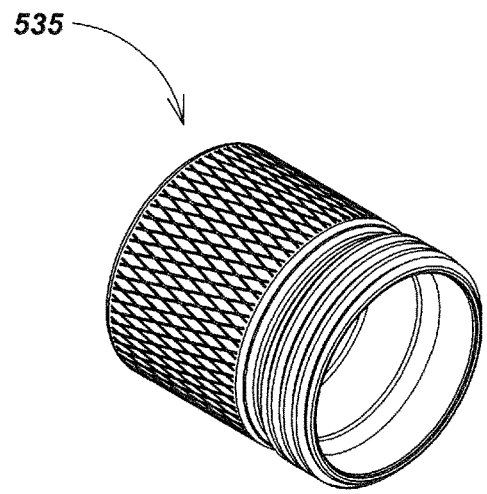
FIG. 6C is a detailed isometric view of a locking sleeve embodiment.
Figure 6D:
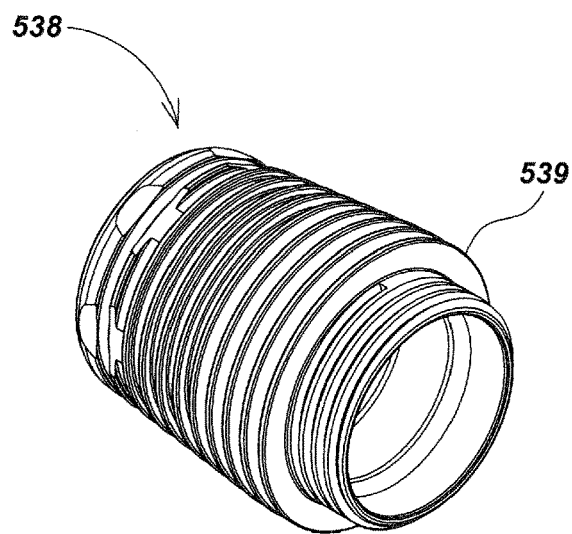
FIG. 6D is a detailed isometric view of an alternative locking sleeve embodiment.
Figure 7:
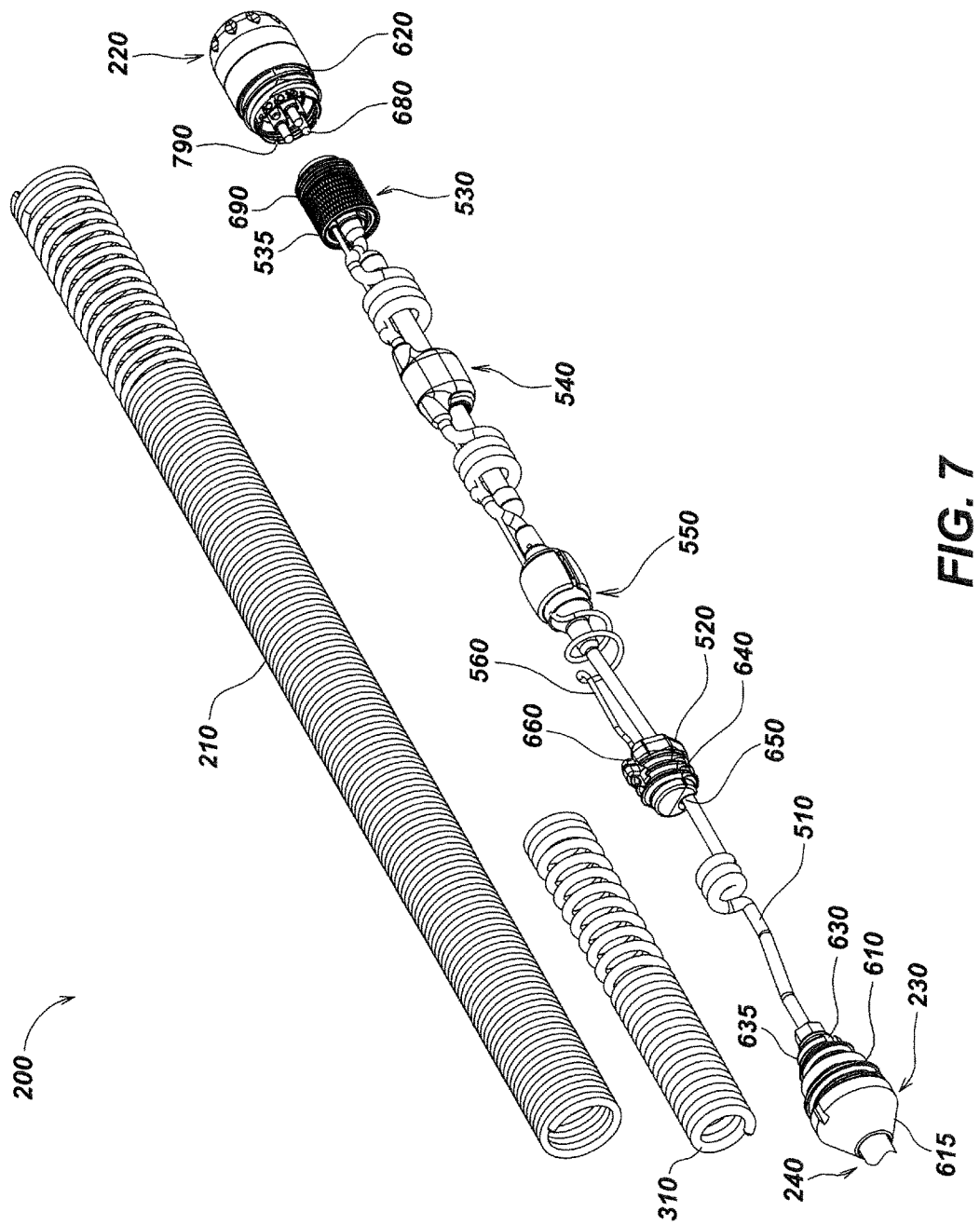
FIG. 7 is a bottom up partially exploded view of the nested spring assembly embodiment of FIG. 2.

Turning to FIG. 5 through FIG. 7, additional details of spring assembly embodiment 200 and associated element embodiments are illustrated. For example, the spring assembly 200 may include one or more connecting wires 510, which may be disposed within the outer coil spring. The connecting wires may pass centrally through the nested spring assembly 200 as shown to extend through the push-cable 240, through the push-cable connector 230, through the nested inner spring 310 positioned within the outer spring 210, through an inner spring mount element 520, through the remainder of the outer spring 210, and to a camera connector 530. Other internal wiring paths may also be used in alternate embodiments. The connecting wires 510 may be used to, for example, provide electrical power and/or communication signals to and from the camera head 220, such as to or from a coupled CCU, wireless transmitter, computer, notebook device, or other electronic computing device or system. In a typical embodiment including a camera, video, images, sound, sensor data, and/or other data or information may be communicated through connecting wires from the camera head 220 to a CCU or other coupled device. Further, control signals or data may be provided from a CCU or other coupled device to the camera head through connecting wires 510, along with electrical power.

In some embodiments, a magnetic field generator or transmitter, such as the sonde 540, may be included within the nested coil assembly. Such a sonde is a magnetic field antenna and may include an associated signal generator, amplifier, and the like. A dipole magnetic field is generated from at or near the distal end of the spring assembly, which may then be sensed by a buried utility locator or other device, typically positioned just above the ground surface above the buried pipe or cavity.

For example, a sonde may be connected to a distal end of a push-cable and electrically coupled to a connecting wire such as one or more of the connecting wires 510 to receive power and/or signals to be converted to radiated magnetic field signals. The radiated magnetic field signals may be simply continuous wave (CW) signals at a particular frequency or frequencies, or may further include modulated data or other information, which may be detected and used by an associated buried utility locator. Additional details of sondes as may be used in various embodiments in conjunction with the disclosure herein are described in, for example, co-assigned U.S. Pat. No. 7,298,126, entitled SONDES FOR LOCATING UNDERGROUND PIPES AND CONDUITS, issued Nov. 20, 2007, and/or U.S. Pat. No. 7,863,885, entitled SONDES FOR LOCATING UNDERGROUND PIPES AND CONDUITS, issued Sep. 29, 2007, and/or U.S. patent application Ser. No. 14/215,290 entitled SONDE DEVICES INCLUDING A SECTIONAL FERRITE CORE, filed Sep. 17, 2014, and/or U.S. patent application Ser. No. 14/027,027, entitled SONDE DEVICES INCLUDING A SECTIONAL FERRITE CORE STRUCTURE, filed Sep. 13, 2013. The content of each of these patents and applications is incorporated by reference herein in its entirety.

A disconnect element 550 comprising an electrical outlet or socket and plug, or other electrical connector device(s), may also be included for removing sections of connecting wires 510 containing or coupled to sonde 540. A safety cable 560 may be coupled from the inner spring mount element 520 to a camera head connector 530 to secure the camera head. This may be done to provide a fail-safe for securing the camera head 220 in place while the system is in use to limit the extension of the nested spring assembly 200 should the camera become caught or snagged, thereby preventing damage or breakage of connecting wires 510. In such embodiments, the nested inner spring 310 may further act as a component of the fail-safe assembly in securing the inner spring mount element 520 with connected safety cable 560 to the push-cable connector 230 and connected push-cable 240. In alternative embodiments, a safety cable may directly or indirectly secure a pipe inspection device such as a camera head to a push-cable via various attachment points.

Both the connecting wires 510 and the safety cable 560 may coil or otherwise stow in various locations within the nested spring assembly 200 so that when the nested spring assembly 200 is bent or flexed the connecting wires 510 and the safety cable 560 have sufficient slack to allow such bending and flexing without damage or breakage.

Still referring to FIG. 6A through FIG. 7, the outer spring 210 may secure to the push-cable connector 230 by mating with a connector outer spring threads feature 610 formed on a rear connector element 615 of the push-cable connector 230. The threads feature may include a threaded element shaped to mate with corresponding threads of the coils of the outer and/or inner coil springs. The opposite end of the outer spring 210 may secure to the camera head 220 by mating with a similar camera spring threads feature 620 formed on a camera head, such as towards the rear of camera head 220 as shown.

Figure 8:
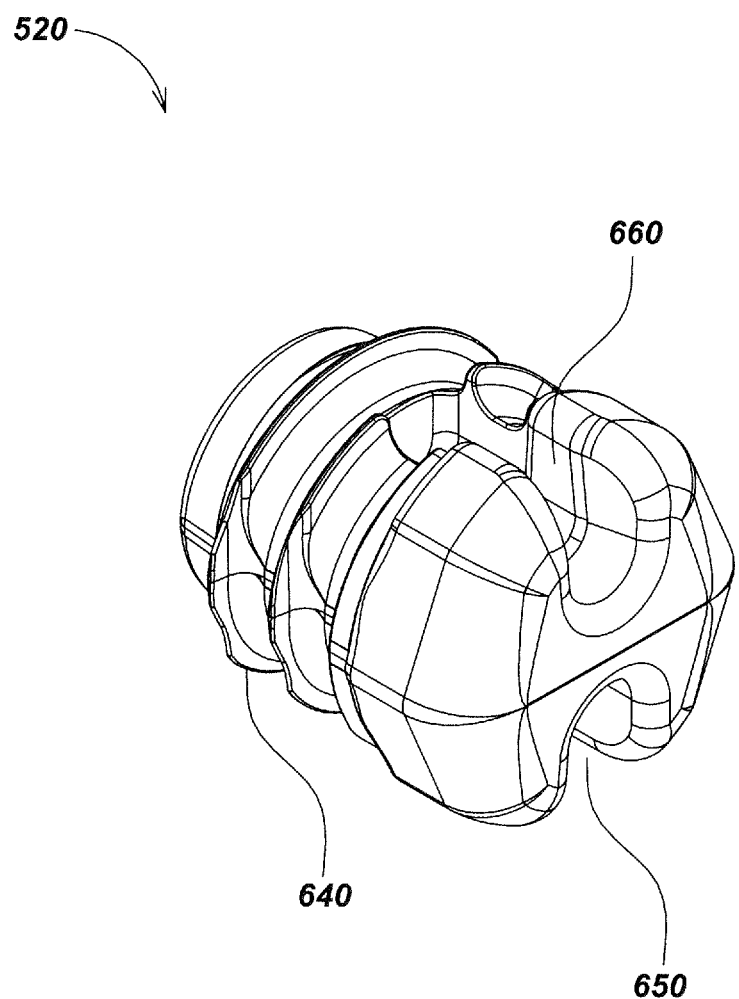
FIG. 8 is a detailed isometric view of an inner spring mount element embodiment.

The nested inner spring 310 may secure to the push-cable connector 230 by mating with a similar connector inner spring threads feature 630 formed on a front connector element 635 on the push-cable connector 230. The inner spring threads feature may similarly include a threaded element shaped to mate with corresponding coils of the outer coiled spring. The opposite end of the nested inner spring 310 may secure to an inner spring mount element 520, as best illustrated in the embodiment of FIG. 8, by mating with an inner spring mounting element threads feature 640 formed towards the rear of the inner spring mount element 520.

As best illustrated in the embodiment of FIG. 6B, the rear connector element 615 and the front connector element 635 may be configured to secure together via left hand threads in assembly. The distal end of the inner spring may be coupled to an inner spring mount element that may further allow connecting wires to pass through. For example, inner spring mount element 520 may be formed with a connecting wire gap 650, allowing the connecting wires 510 of FIG. 6A to pass through the inner spring mount element 520, and may include a safety cable connector attachment or feature 660 allowing the safety cable 560 of FIG. 6A through FIG. 7 to connect to the inner spring mount element 520.

Referring back to FIG. 6A through FIG. 7, the camera connector 530 may be formed with a camera connector female plug 670 (as shown in FIG. 6A) and locking sleeve 535 (best illustrated in FIG. 6C), which may mate with a camera male pin connector 680 on the camera head 220 so as to power and communicate signals to and from the camera head 220. In some embodiments, an alternative locking sleeve 538 as illustrated in FIG. 6D may be used. The alternative locking sleeve 538 may be formed with a series of annular fins 539 which may aid in dissipating heat away from a coupled camera head. Camera connector threads 690 formed on the front outer circumference of the camera connector 530 may further mate with camera head threads 790 as shown in FIG. 7, and may be formed within the back of the camera head 220 to secure the camera connector 530 to the camera head 220.

Figure 9:
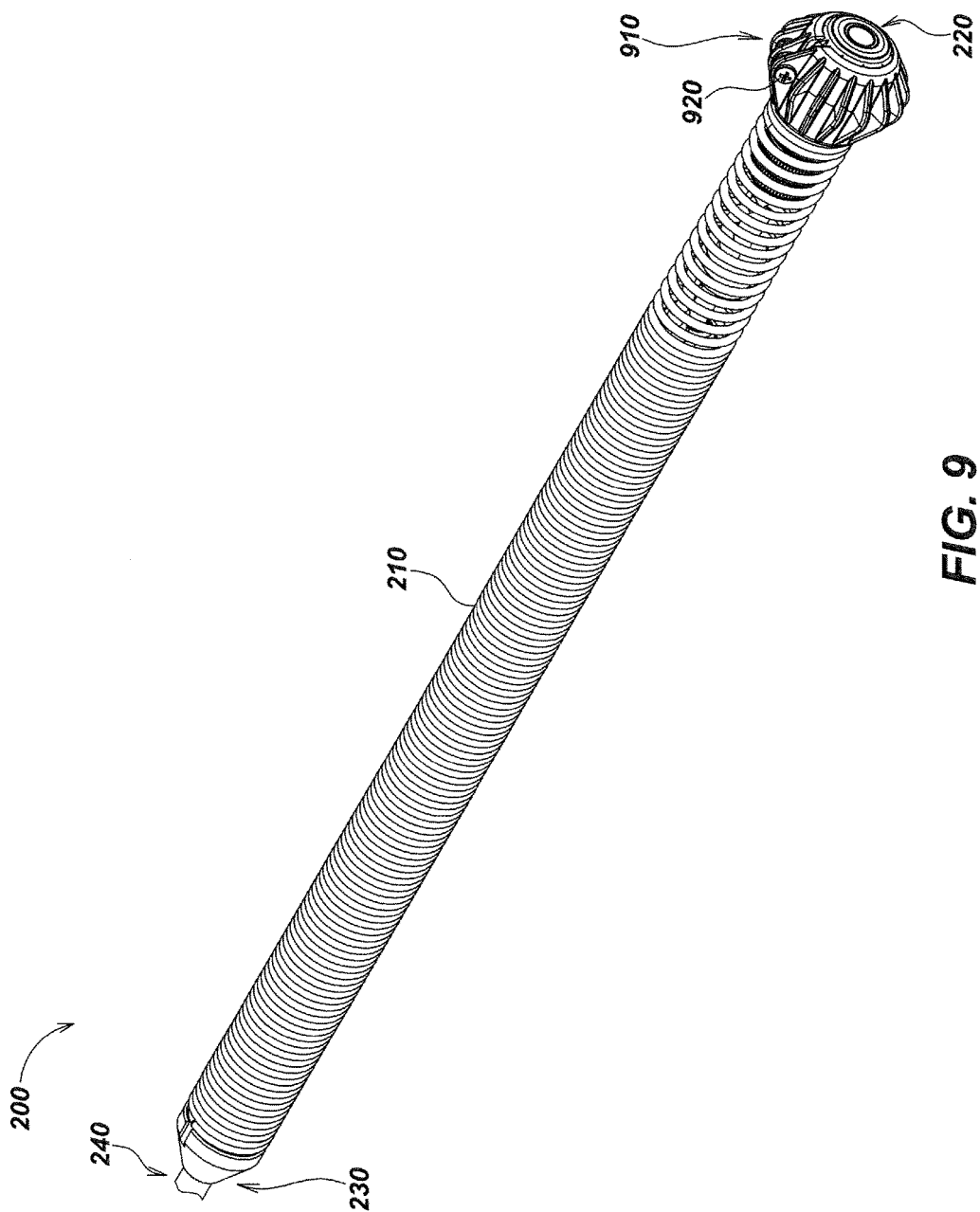
FIG. 9 is an isometric view of the nested spring assembly embodiment of FIG. 2 with a coupled camera guide embodiment.
Figure 10A:
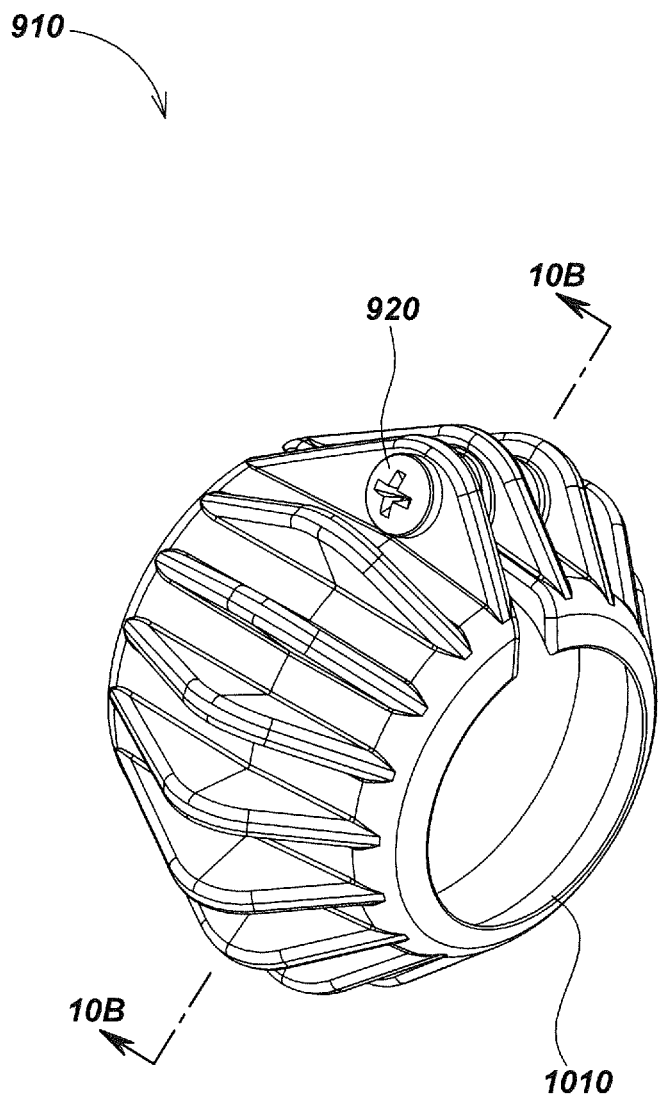
FIG. 10A is a detailed isometric view of the camera guide embodiment of FIG. 9.
Figure 10B:
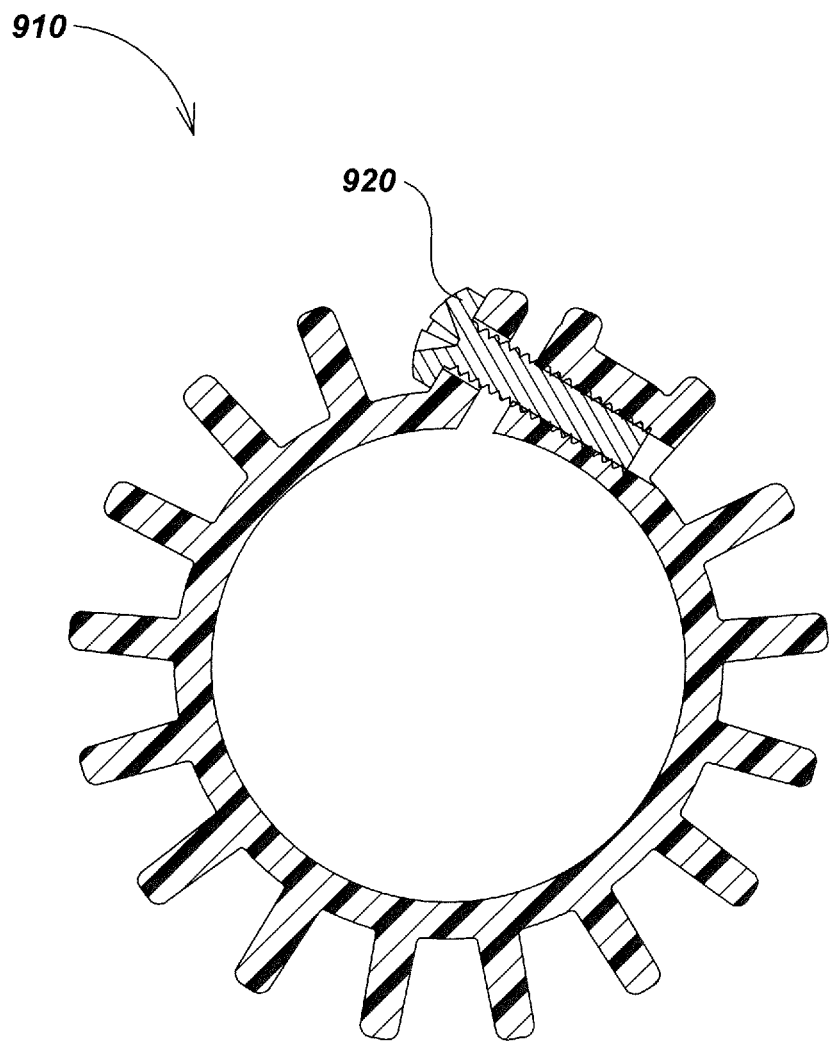
FIG. 10B is a sectional view of the camera guide embodiment of FIG. 9.

Turning to FIG. 9 through FIG. 10B, a camera guide, such as the camera guide embodiment 910 as shown, may be coupled at a distal end of the nested spring assembly embodiment 200 (as shown in FIG. 9) on or adjacent to a camera head, such as camera head 220 as shown. The camera guide 910 may be used to aid in centering the camera head 220 within a pipe. Details of various camera guide embodiments as may be used in conjunction with the disclosures herein are described in, for example, co-assigned U.S. Pat. No. 6,862,945, entitled CAMERA GUIDE FOR VIDEO PIPE INSPECTION SYSTEM, issued Mar. 8, 2005, as well as U.S. Pat. No. 8,540,429, entitled SNAP-ON PIPE GUIDE, issued Sep. 24, 2013. The content of each of these patents and applications is incorporated by reference herein in its entirety. The camera guide 910 may couple tightly to the camera head 220 and/or to coils of the push-cable assembly, and may comprise materials with high thermal conductivity such as, but not limited to, aluminum, stainless steel, thermally conductive plastics or ceramics, composite materials, or other materials suited to aid in extracting heat away from the camera head 220.

In assembly, the camera head 220 may be fitted through a central opening within the camera guide 910. A screw 920 along one side of the camera guide 910 may be tightened to secure the camera guide 910 to the camera head 220. As best illustrated in FIG. 10A and FIG. 10B, a lip 1010 may be formed on the outer end of the camera guide 910 so as to limit rearward travel and set position on the camera head 220 (as shown in FIG. 9).

Figure 11:
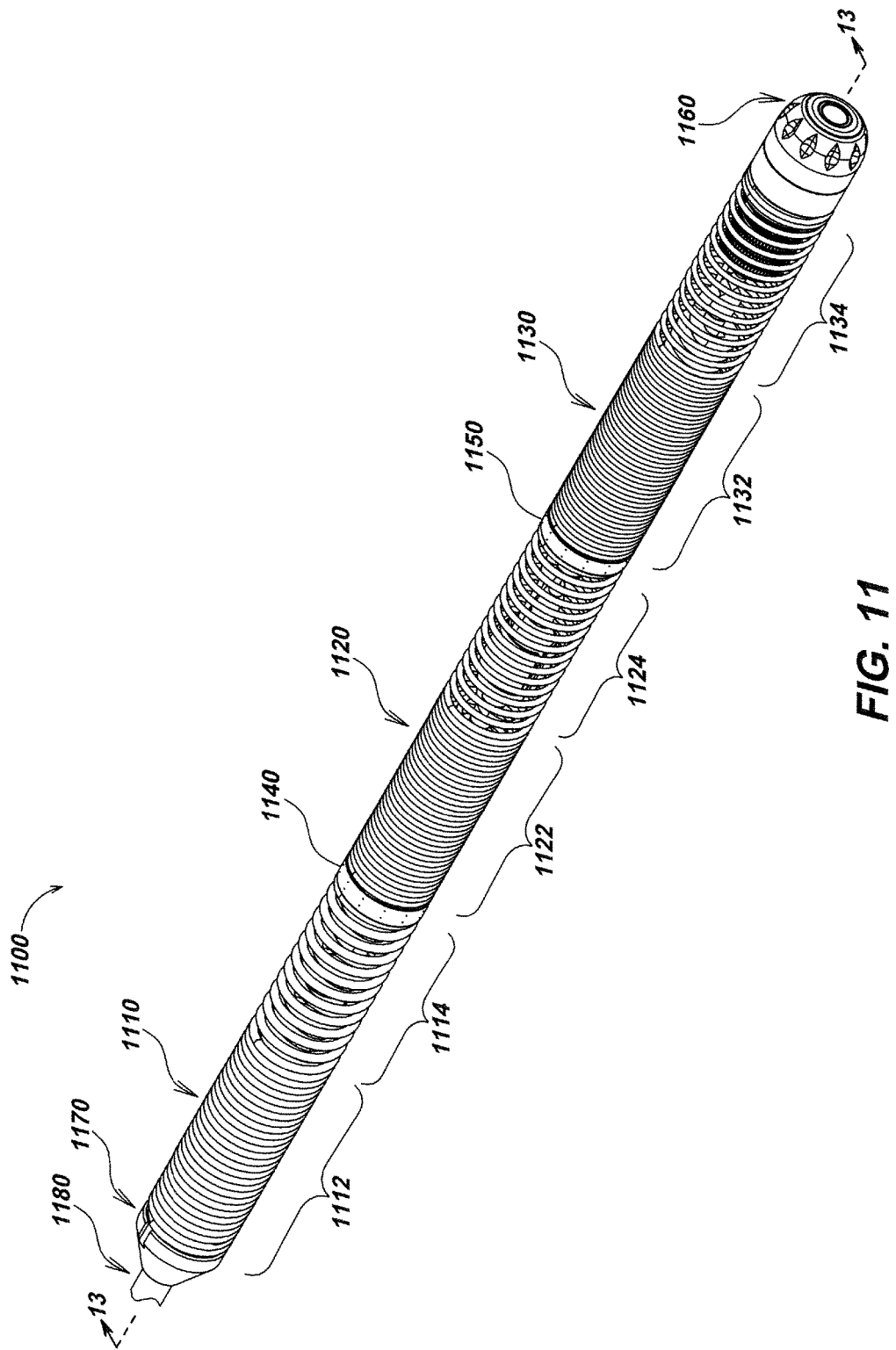
FIG. 11 is an isometric view of an alternative spring assembly embodiment with an attached camera head and push-cable.
Figure 12:
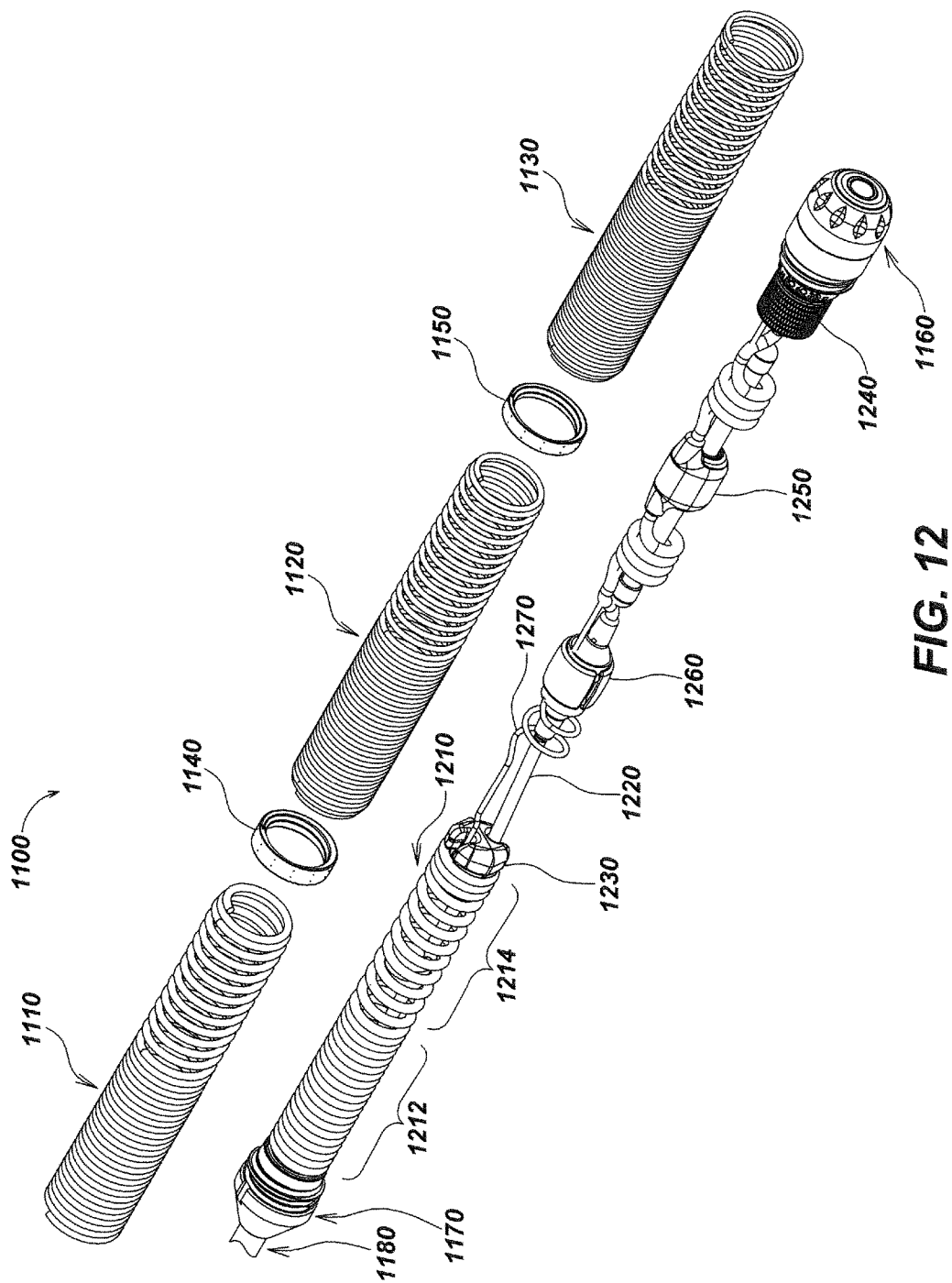
FIG. 12 is a partially exploded view of the embodiment of FIG. 11.
Figure 13:
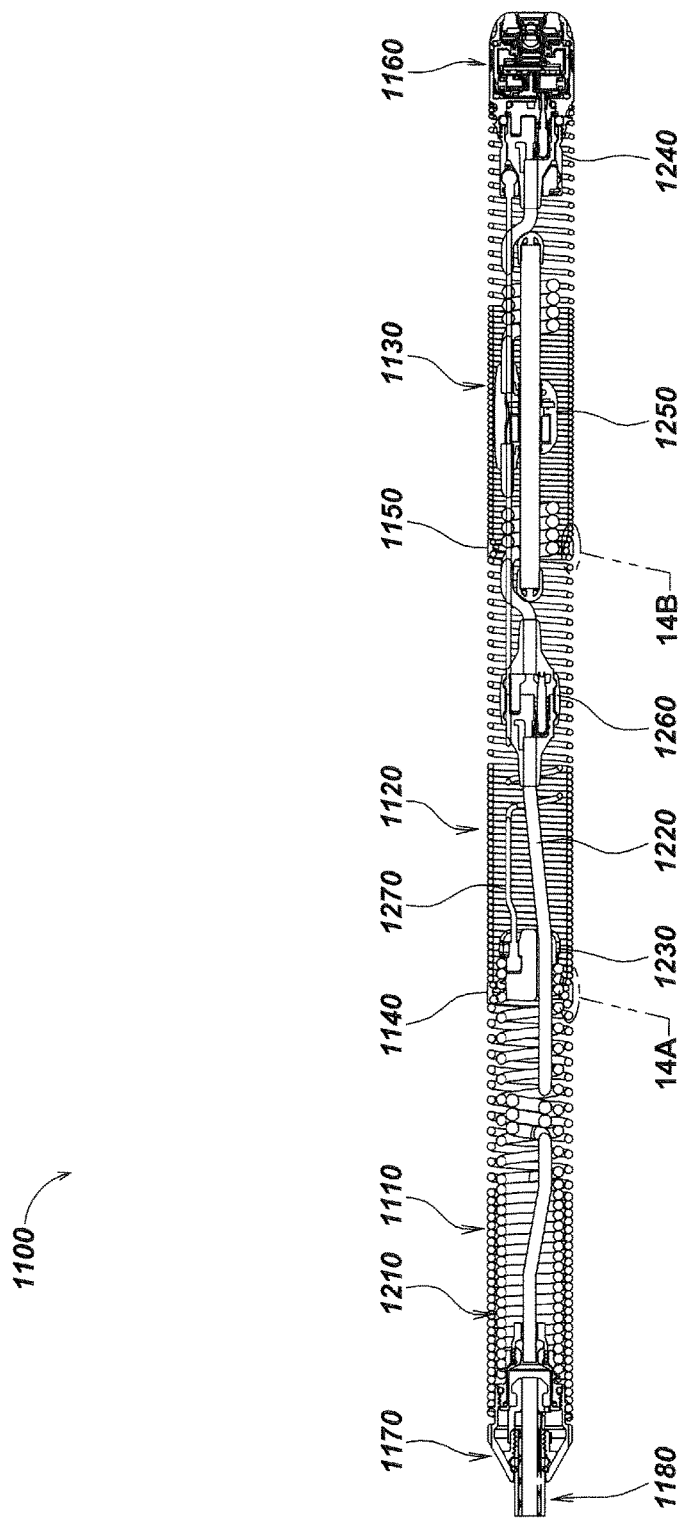
FIG. 13 is a sectional view of the embodiment of FIG. 11 taken along line 13-13.

Turning to FIG. 11 through FIG. 13, details of another spring assembly embodiment 1100 having a plurality of spring elements for providing variable flexibility are illustrated. As shown in FIG. 11, coiled spring assembly embodiment 1100 may include a rear or proximal outer spring element 1110, a middle outer spring element 1120, and a front or distal outer spring element 1130 (or, in other embodiments, fewer or more spring elements). A first section on each spring of the rear outer spring element 1110, the middle outer spring element 1120, and the front outer spring element 1130 may be formed with a second section of each spring having non-gapped or "closed" windings (i.e. adjacent coils substantially in contact in a relaxed state), while the first section of each spring has gapped or "open" or spaced windings. Other embodiments (not shown) may use spring elements having sections with varying materials, varying coil diameters or cross-sectional shapes, varying coil wire cross-sectional areas or sizes, varying pitch, varying material properties, varying coil-to-coil spacing, and the like.

As illustrated in FIG. 11, the rear outer spring 1110 may be formed with a rear outer spring non-gapped or "closed" section 1112 and a rear outer spring gapped or "open" section 1114. The middle outer spring 1120 may be formed with a middle outer spring non-gapped section 1122 and a middle outer spring gapped section 1124. Furthermore, the front outer spring 1130 may be formed with a front outer spring non-gapped section 1132 and a front outer spring gapped section 1134.

As illustrated in FIG. 12, the spring assembly 1100 may further include an inner, nested spring 1210 that secures fully or partially within the rear outer spring 1110 and may span some or all of the length of the outer spring. In various alternative embodiments, an inner spring, such as the inner spring 1210, may be of various lengths or may be the same length as its surrounding outer spring, such as the rear outer spring 1110. The inner spring 1210, as illustrated in FIG. 12, may also have a rear section with non-gapped or closed windings, such as the illustrated inner spring non-gapped section 1212, and a front section with gapped or pen windings, such as the inner spring gapped section 1214. The front gap sections on each spring may bend and flex with greater ease than the non-gapped sections of each spring due to the gap between spring coils. Other embodiments (not shown) may use inner springs having sections with varying materials, varying coil diameters or coil wire cross-sectional areas or sizes or shapes, varying pitch, varying material properties, and the like so as to vary the flexing or bending of the spring.

A rear inline coupler 1140 may be secured about the front of the rear outer spring 1110 and the rear of the middle outer spring 1120 connecting the rear outer spring 1110 and the middle outer spring 1120. A front inline coupler 1150 may be secured about the front of the middle outer spring 1120 and the rear of the front outer spring 1130, connecting the middle outer spring 1120 and the front outer spring 1130. In assembly, electron beam welding or other binding or joining techniques may be used to secure the springs to the inline couplers.

In embodiment 1100, a smaller gauge of wire may be used to form the middle outer spring 1120 than the gauge of wire used to form the rear outer spring 1110. Furthermore, a smaller gauge of wire may be used to form the front outer spring 1130 than the gauge of wire used to form the middle outer spring 1120. The different gauge wires used to form each spring in combination with the gapped and non-gapped sections of each spring may allow for increasing ease in ability to bend and flex from the rear to the front of the spring assembly 1100 so as to provide variable flexibility.

As noted previously, the rear outer spring 1110 may encapsulate an inner spring 1210 (FIG. 12). Additional sections of successive flexibility may be used in the area of the rear outer spring 1110. A camera head 1160, such as the example camera heads described in the aforementioned incorporated patent applications or other camera heads as are known or developed in the art, may be secured about the front-most end of the spring assembly 1100. A push-cable connector 1170 may be secured about the rearmost end of the spring assembly 1100, securing a push-cable 1180 to the spring assembly 1100. The winding tension within each spring section may be varied to increase spring flexibility moving forward from the push-cable 1180 to the camera head 1160 so as to provide varying flexibility.

One or more connecting wires may be positioned within the outer coiled spring in some embodiments. For example, as illustrated in FIG. 12 and FIG. 13, one or more connecting wires 1220 may pass centrally through the spring assembly 1100 extending from within the push-cable 1180, through the push-cable connector 1170, through the nested inner spring 1210 positioned within the rear outer spring 1110, through an inner spring mount element 1230, through the remainder of the spring assembly 1100 and to a camera connector 1240. Alternate internal wire routing paths may also be used in alternate embodiments. The connecting wires 1220 may be used to provide electrical power and/or signal connections to and from the camera head 1160. For example, signal connections may control signaling for controlling the operation of the camera head and any internal circuit elements and/or mechanical movement or articulation elements, as well as for transferring images, videos, or other data or information from the camera head to a coupled CCU, notebook computer, tablet, cellular phone, or other electronic computing device or system, where it may be stored in a memory, displayed, transferred, and/or otherwise be used or processed.

In some embodiments, a transmitter such as the sonde 1250 may be included on or coupled to connecting wires such as the connecting wires 1220. Descriptions of example sondes as may be used in conjunction with embodiments in conjunction with the disclosures herein are described in the incorporated patent applications. A disconnect element 1260 may also be included for removing the section of connecting wires 1220 containing the sonde 1250.

A safety cable 1270 may connect from the inner spring mount element 1230 to the camera connector 1240, and may function as a fail-safe for securing the camera head 1160 in place while the system is in use. In such embodiments, the inner spring 1210 may further be a component of the fail-safe assembly in securing the inner spring mount element 1230 with connected safety cable 1270 to the push-cable connector 1170 and connected push-cable 1180 to prevent damage to connecting wires 1220 due to breakage or excessive stretching, bending, and the like.

Figure 15:
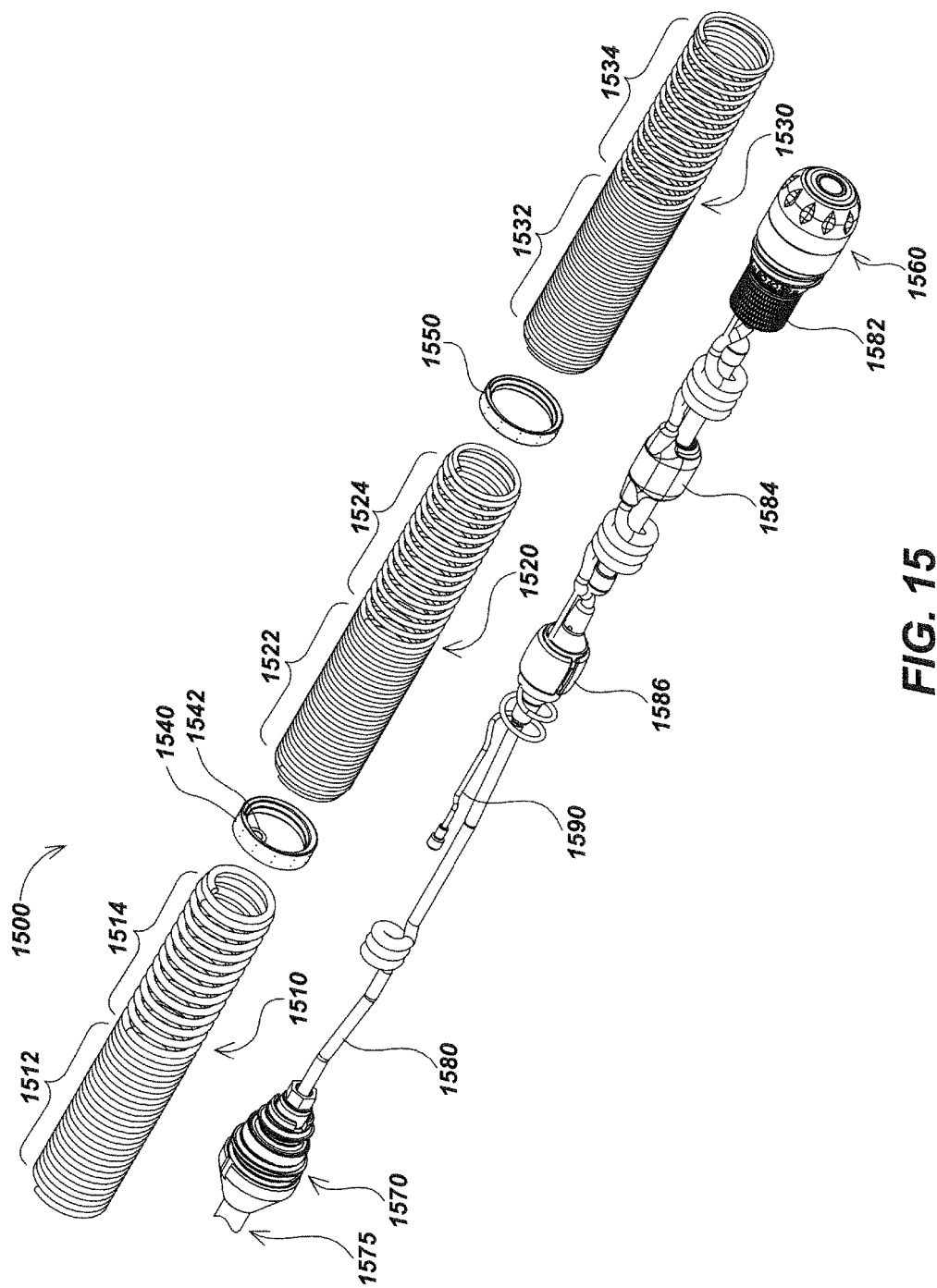
FIG. 15 is a partially exploded view of an alternative spring assembly embodiment with an attached camera head and push-cable.
Figure 16:
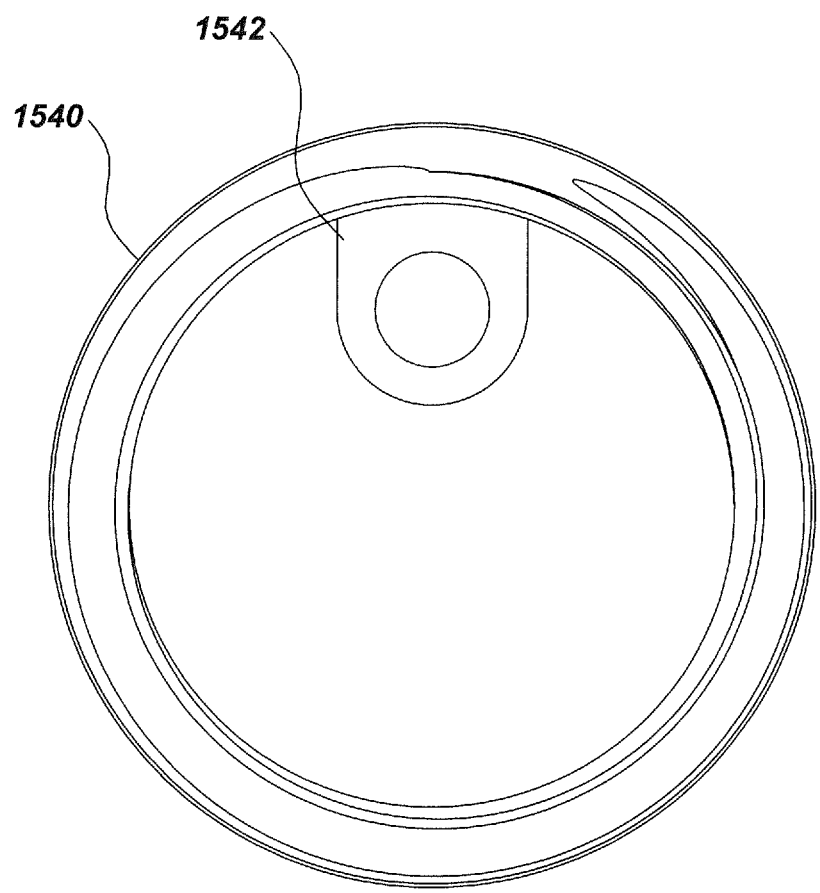
FIG. 16 is a detailed view of the rear inline spring coupler from the embodiment of FIG. 15.

In alternate embodiments, a safety cable may directly or indirectly secure a pipe inspection device such as a camera head, jetting or cutting tool, or other device or apparatus to a push-cable or to an inline coupler, such as the rear inline coupler 1540, via a safety cable connector feature 1542 as best illustrated in the embodiment of FIG. 15. Both the connecting wires 1220 and the safety cable 1270 may coil or stow in various locations within the spring assembly 1100 such that when the spring assembly 1100 is bent or flexed the connecting wires 1220 and the safety cable 1270 provide sufficient slack to allow such bending and flexing.

Figure 14A:
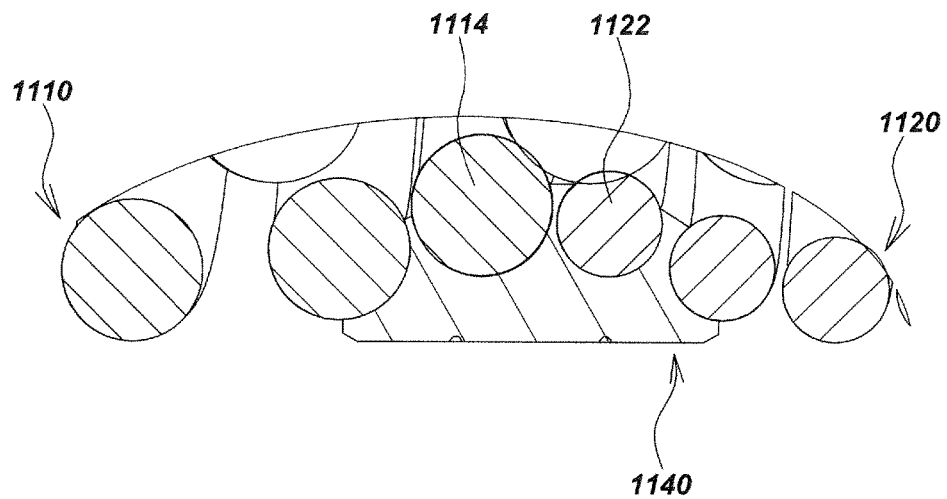
FIG. 14A is a partial sectional view of the embodiment of FIG. 13 illustrating the relationship between a rear inline coupler and connected springs.

Turning to the embodiment of FIG. 14A, the rear inline coupler 1140 may be secured to the end coils from the rear outer spring gapped section 1114 of the rear outer spring 1110 and the end coils on the middle outer spring non-gapped section 1122 of the middle outer spring 1120. The end coils of each spring may taper inward where they are made to secure to the rear inline coupler 1140. The rear outer spring 1110 and the middle outer spring 1120 may be secured to the rear inline coupler 1140 through mechanical attachment means, welds, adhesives, or other methods known or developed in the art. A continuous bead weld, friction welding, and/or induction welding may also be used.

Figure 14B:
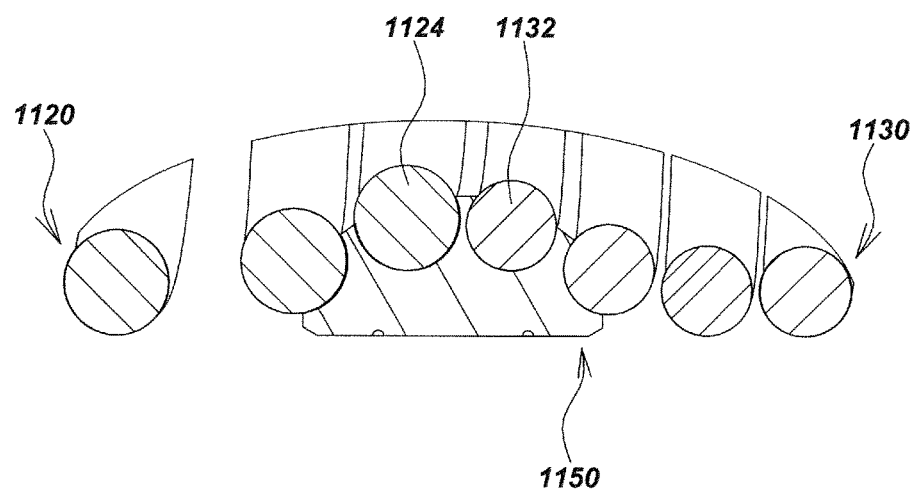
FIG. 14B is a partial sectional view of the embodiment of FIG. 13 illustrating the relationship between a front inline coupler and connected springs.

Turning to FIG. 14B, the front inline coupler 1150 may secure to the end coils from the middle outer spring gapped section 1124 of the middle outer spring 1120 and the end coils on the front outer spring non-gapped section 1132 of the front outer spring 1130. The end coils of each spring may taper inward where they are secured to the front inline coupler 1150. The middle outer spring 1120 and the front outer spring 1130 may secure to the front inline coupler 1150 through welds, adhesives, or any other known or unknown methods.

Figure 14C:
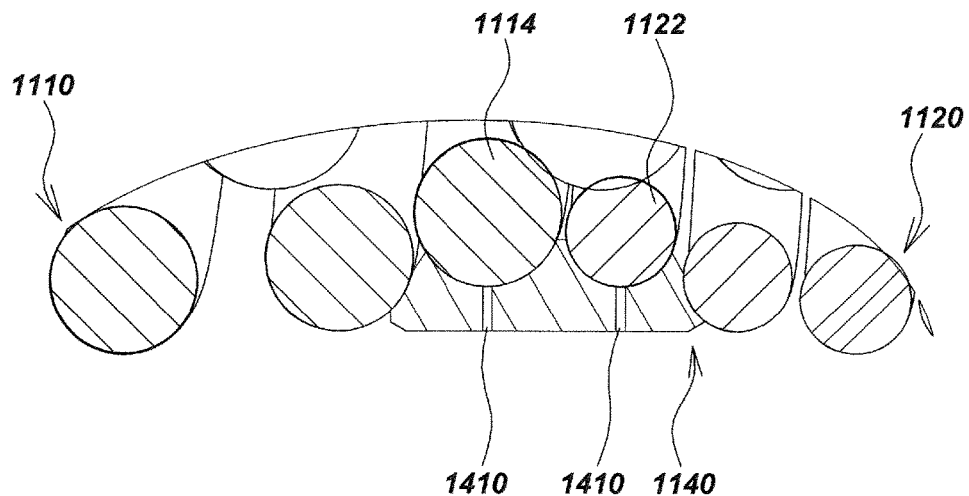
FIG. 14C and FIG. 14D illustrate details of formation of inline couplers relative to spring circumference.
Figure 14D:
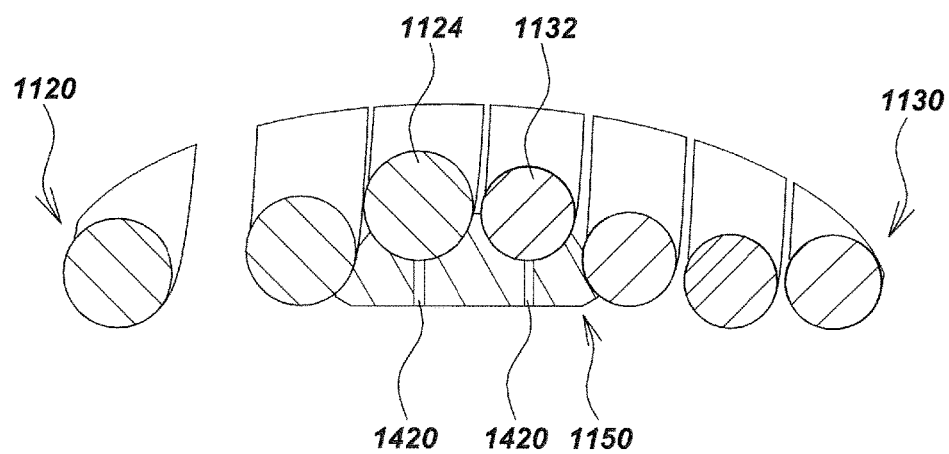

Turning to FIG. 14C and FIG. 14D, in some embodiments, the rear inline coupler 1140 and/or the front inline coupler 1150 may be formed so as not to protrude past the circumference of each spring. In some such embodiments, electron beam welding, as illustrated by the electron beam welding spots 1410 on the rear inline coupler 1140 and the electron beam welding spots 1420 on the front inline coupler 1150, may be used to secure the springs to their respective inline couplers.

Turning to FIG. 15, a spring assembly embodiment 1500 in accordance with aspects of the present disclosure may include a rear outer spring 1510, a middle outer spring 1520, and a front outer spring 1530, each with a gapped and non-gapped section similar to the springs of the spring assembly embodiment 1100 of FIG. 11 through FIG. 13. The rear outer spring 1510 may be formed with a rear outer spring non-gapped or closed section 1512 and a rear outer spring gapped or open section 1514. The middle outer spring 1520 may be formed with a middle outer spring non-gapped section 1522 and a middle outer spring gapped section 1524. Furthermore, the front outer spring 1530 may be formed with a front outer spring non-gapped section 1532 and a front outer spring gapped section 1534. In some embodiments, such as the spring assembly embodiment 1500, the nested inner spring may be omitted.

A rear inline coupler 1540 may secure about the front of the rear outer spring 1510 and the rear of the middle outer spring 1520, connecting the rear outer spring 1510 and the middle outer spring 1520. A front inline coupler 1550 may secure about the front of the middle outer spring 1520 and the rear of the front outer spring 1530, connecting the middle outer spring 1520 and the front outer spring 1530. In assembly, electron beam welding or various other methods may be used to secure the springs to the inline couplers. In the embodiment 1500, a smaller gauge of wire may be used to form the middle outer spring 1520 than the rear outer spring 1510. Furthermore, a smaller gauge of wire may be used to form the front outer spring 1530 than the middle outer spring 1520. The different gauge wire used to form each spring, in combination with the gapped and non-gapped sections of each spring, may allow for increasing ease in ability to bend and flex from the rear to the front of the spring assembly 1500 to provide variable flexibility. A camera head 1560, such as a camera head as described in the incorporated applications or another camera head, may secure about the frontmost end of the spring assembly 1500. A push-cable connector 1570 may secure about the rearmost end of the spring assembly 1500, securing a push-cable 1575 to the spring assembly 1500.

As further illustrated in FIG. 15, connecting wires 1580 may pass centrally through the spring assembly 1500 extending from within the push-cable 1575, through the push-cable connector 1570, through the center of the spring assembly 1500 and to a camera connector 1582. Other wire routings may be used in alternate embodiments. The connecting wires 1580 may be used to power and communicate signals to and from the camera head 1560. In some embodiments, a transmitter, such as the sonde 1584 as shown, may be included on or coupled to connecting wires, such as the connecting wires 1580. Further details regarding example sondes as may be used in conjunction with the disclosures herein may be found in incorporated applications. A disconnect 1586 may also be included for removing the section of connecting wires 1580 containing the sonde 1584. A safety cable 1590 may connect from the camera connector 1582 to a safety cable connector feature 1542 on the rear inline coupler 1540 as best illustrated on FIG. 16 and may function as a fail-safe for securing the camera head 1560 in place while the system is in use. Both the connecting wires 1580 and the safety cable 1590 may coil in various locations within the spring assembly 1500 such that when the spring assembly 1500 may be made to bend and flex, the connecting wires 1580 and the safety cable 1590 may both provide sufficient slack to allow such bending and flexing.

Figure 17A:
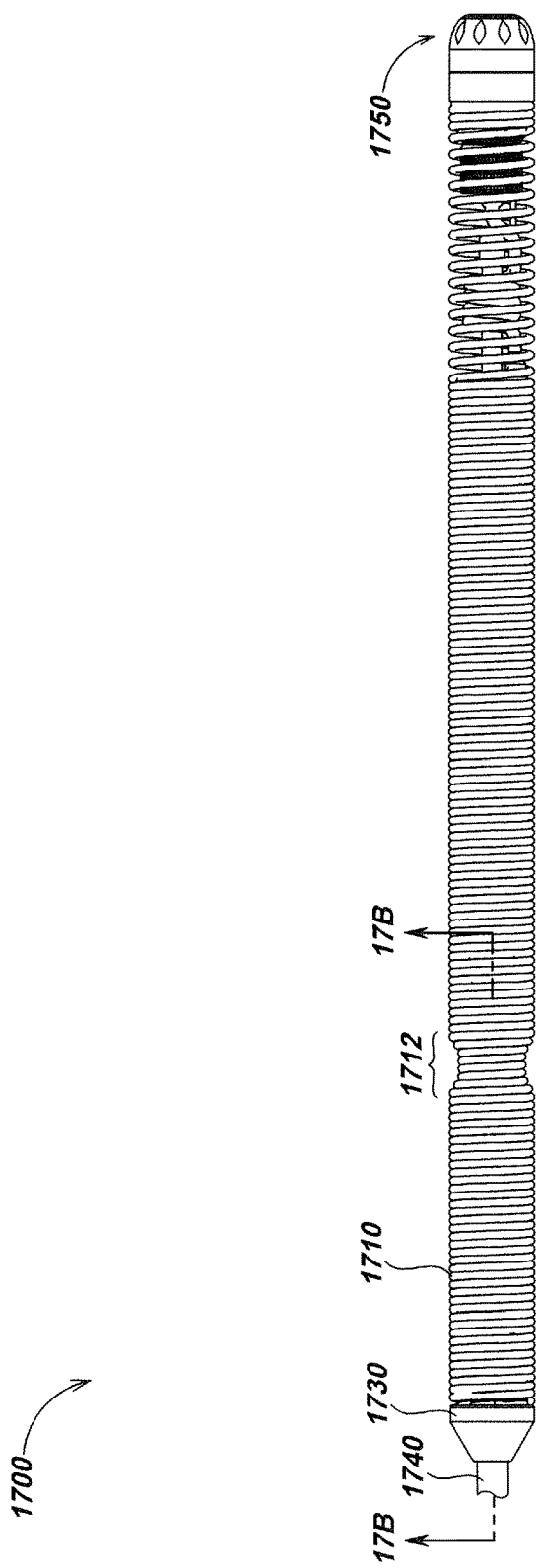
FIG. 17A illustrates an alternative embodiment of a spring assembly.
Figure 17B:
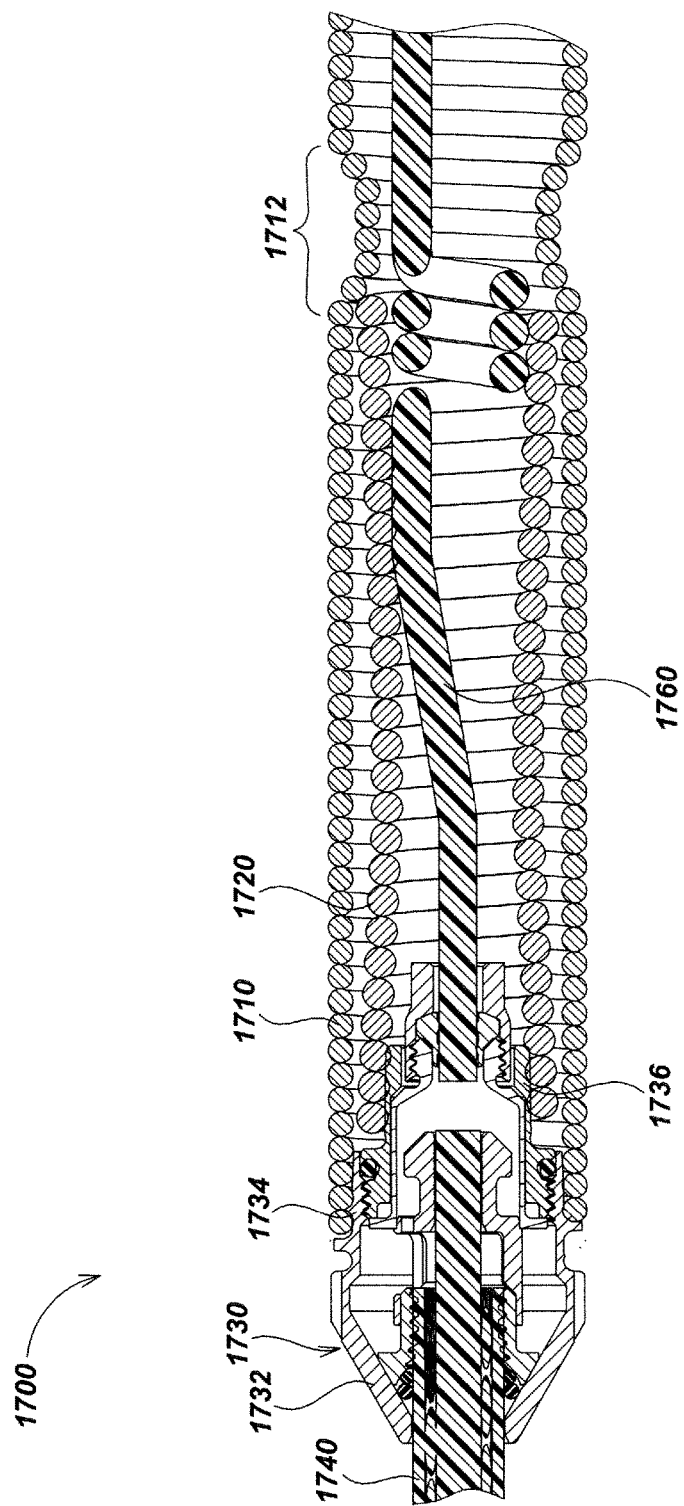
FIG. 17B is a sectional view along line 17B-17B of the embodiment of FIG. 17A.

Turning to FIG. 17A and FIG. 17B, an alternative spring assembly embodiment 1700 is illustrated. Spring assembly embodiment 1700 may include an outer spring 1710 which may enclose an inner spring 1720, such as shown in cross-section in FIG. 17B. The outer spring may include a first section having a first coil diameter, as well as a second section, such as a reduced diameter section 1712 as shown, having one or more coils with a diameter less than those of the first section. In an exemplary embodiment as shown in FIG. 17A and FIG. 17B, most of the spring has coils with the larger diameter, while a small portion of the coil (i.e. section 1712) has coils having a smaller diameter. However, in other embodiments, various different coil diameters in the outer and inner sections may be used, as may be coils of different material or property types, cross-sectional shapes, coil wire gauges, and the like.

The inner spring 1720 (as shown in FIG. 17B) may be positioned as shown between reduced diameter section 1712 on the outer spring 1710 and a push-cable connector 1730, where section 1712 includes a plurality of coils (in the reduced diameter section) having a diameter less than that of the remainder of the outer coil spring 1710.

Push-cable connector 1730 may be used to secure a push-cable 1740 to the spring assembly 1700 at a distal or rear-most end. A camera head 1750 (as shown in FIG. 17A) may be secured about a front-most or distal end of the spring assembly 1700. As best illustrated in FIG. 17B, the push-cable connector 1730 may include a rear connector element 1732, which may have a threaded feature 1734, and a front connector element 1736. The rear connector element 1732 and/or the front connector element 1736 may have left-handed threads and be secured with the left handed threads in assembly.

The threaded feature 1734 on the rear connector element 1732 may be configured to mate with the end windings of the outer spring 1710, securing the push-cable connector 1730 to the spring assembly 1700. Unlike the front connector element 635 of FIG. 6, the front connector element 1734 from FIG. 17B may omit the threaded feature for securing the inner spring 1720.

In some embodiments, such as with the spring assembly embodiment 1700, the end winding or windings of an inner spring may be tapered to have a greater diameter than the middle windings as shown in FIG. 17B. For example, the end windings of the inner spring 1720 may be of a greater diameter than windings along the midsection of the inner spring 1720. In use, this may aid in preventing the windings of the outer spring 1710 from snagging on windings of the inner spring 1720. Connecting wires 1760 may be positioned within the outer spring, and may pass from the push-cable 1740 through the push-cable connector 1730 and be used to provide power and/or signaling to a camera head such as the camera head 1750 of FIG. 17A. Other internal routings may be used in alternate embodiments.

Some embodiments may include inner and/or outer coil springs where the cross-section and/or effective gauge of the spring or springs may be varied in sections of the spring. For example, smaller wire cross-sections may be used in the coils towards one end of the spring in some embodiments. Different wire cross-sectional shapes may also be used in some embodiments so that the coil cross-section changes along the spring. In some embodiments the coils may be of an increasingly larger cross-section towards one end. Such a configuration may be used to allow the spring to bend and flex with less resistance on the end with smaller cross-section wire than on the end with the larger cross-section wire. In manufacture, such sections may be created by removing material from the spring, for instance, through the use of a lathe or electrical discharge machining. In some embodiments, tapering the cross-section size of wire in each coil may allow for a smooth transition in the force required to cause the spring to bend and flex. In some embodiments, springs made of wire having varying cross-sectional shapes may be used so that the cross-sectional shape changes across the length of the spring to provide varying flexibility.

Figure 18:
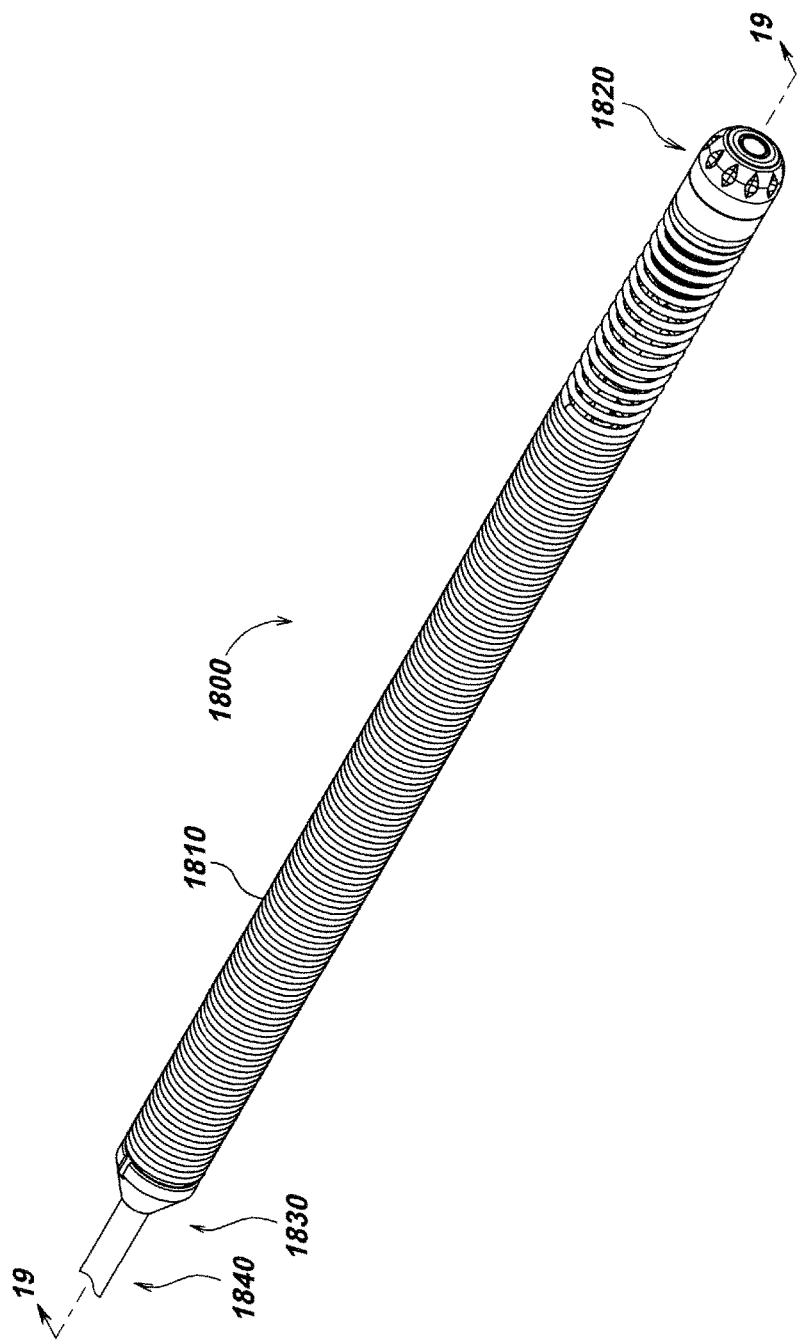
FIG. 18 is an isometric view of a nested spring assembly embodiment with an attached camera head.
Figure 19:
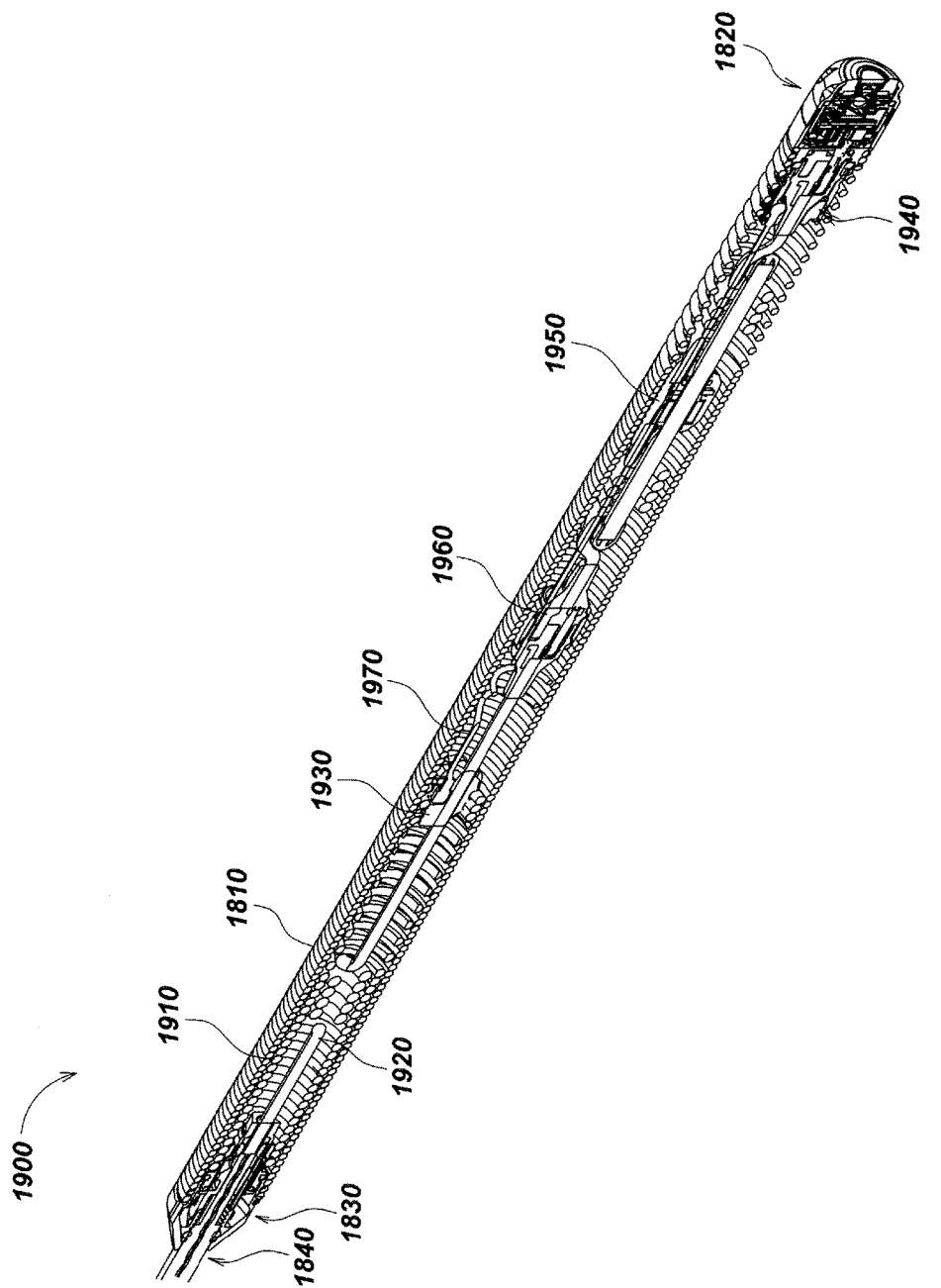
FIG. 19 is a sectional view of the nested spring assembly embodiment of FIG. 18 taken along line 19-19.

Turning to FIG. 18 and FIG. 19, another spring assembly embodiment 1800 in accordance with certain aspects of the disclosure is illustrated. Embodiment 1800 may include an outer coiled spring 1810, which may enclose or contain at least a portion of a nested inner spring 1910, such as shown in cutaway in FIG. 19. A camera head 1820 (and/or other elements, such as LED lights, cutting tools or jets for pressure cleaning, etc., not shown) may be secured about a distal or front-most end of the nested spring assembly 1800. A push-cable connector element 1830 may be coupled to the rear-most or proximal end of the nested spring assembly 1800 to secure a push-cable 1840 to the nested spring assembly 1800.

Turning to FIG. 19, one or more connecting wires 1920 may be disposed within the outer coil spring 1810. The connecting wires 1920 may pass centrally through the nested spring assembly 1800 as shown to extend through the push-cable 1840, through the push-cable connector 1830, through the nested inner spring 1910 positioned within the outer spring 1810, through an inner spring mount element 1930, through the remainder of the outer spring 1810, and to a camera head connector 1940. Other internal routing paths may also be used in various embodiments. The connecting wires 1920 may be used to provide electrical power and/or communicate signals to and from the camera head 1820 as described previously herein, such as from a coupled CCU wireless transmitter, computer, notebook device, or other electronic computing device or system.

A disconnect element 1960 may also be included for removing sections of connecting wires 1920 containing the sonde 1950. A safety cable 1970 may be coupled from the inner spring mount element 1930 to a camera head connector 1940, and may function as a fail-safe for securing the camera head 1820 in place while the system is in use by limiting the extension of the nested spring assembly 1800 should the camera become caught or snagged, thereby preventing damage or breakage of connecting wires 1920. In such embodiments, the nested inner spring 1910 may further act as a component of the fail-safe assembly in securing the inner spring mount element 1930 with connected safety cable 1970 to the push-cable connector 1830 and connected push-cable 1840.

Both the connecting wires 1920 and the safety cable 1970 may coil or stow in various locations within the nested spring assembly 1800 such that when the nested spring assembly 1800 is bent or flexed the connecting wires 1920 and the safety cable 1970 have sufficient slack to allow such bending and flexing without damage or breakage.

As noted previously, in some embodiments the coil wire cross-sectional area and/or shape may be varied across the length of the spring, either continuously or variably. For example, a spring element of a spring assembly, such as an outer spring or one or more nested inner springs as described previously herein, may have lengthwise sections with coils having varying cross-sectional areas and/or varying cross-sectional shapes. In addition, lengthwise sections of the springs may have varying open and closed-coil sections such as described previously herein. Such springs may be wound by coiling wires having circular or rectangular or other cross-sectional areas, and the cross-sectional area and/or shape may be varied across the spring's length by removing material from the coils by machining or other processes. Alternately, wires having different cross-sectional shapes and/or areas may be formed with dies or other methods and then wound into coiled springs.

Figure 20:
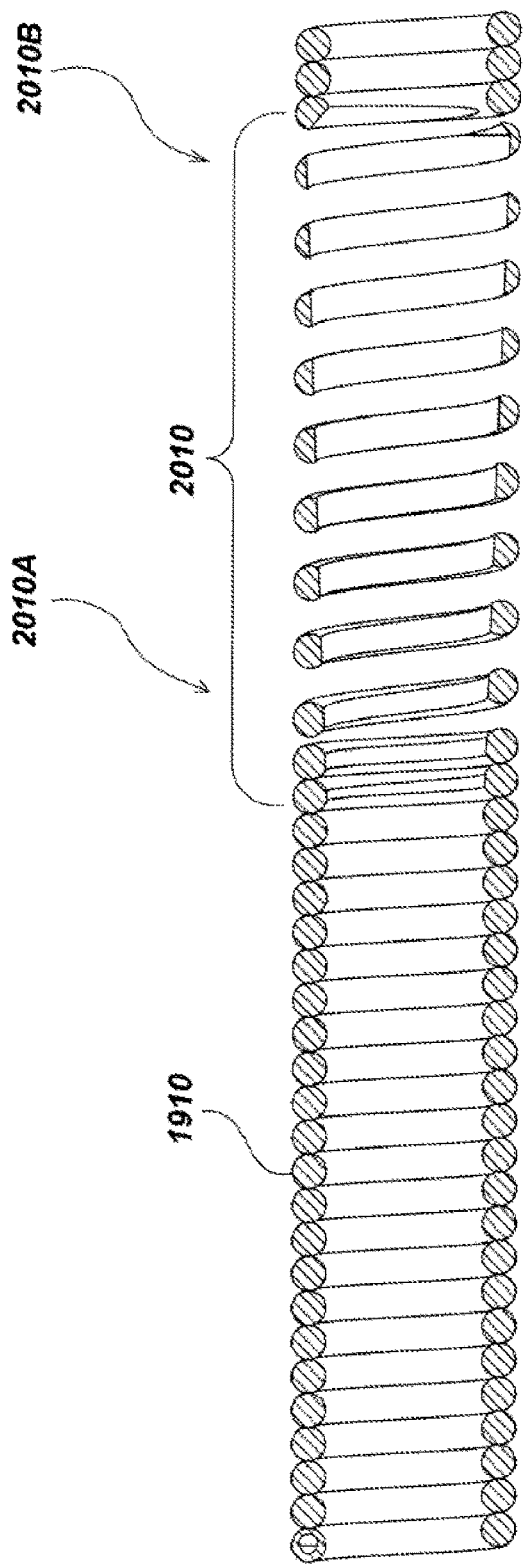
FIG. 20 is a detailed sectional view of a nested inner spring from FIG. 19.

In one example embodiment as illustrated in FIG. 20, a nested inner spring 1910 (as seen in cutaway in FIG. 19) may be formed with a tapered flex section 2010 having a varying cross-sectional area and shape. The spring cross-section may be varied in manufacturing in various ways, such as through dies, milling or cutting, and the like, or the coils may be formed as a wire or ribbon with varying cross-sectional area and shape and then wound into a coiled spring. In an exemplary embodiment, a boring or drilling operation in the internal diameter along the tapered flex section 2010 may be done to increase the amount of material removed from the coils progressively towards a forward or distal end. For example, material may be progressively removed from the nested inner spring 1910 towards the forward end of the tapered flex section 2010 as shown so that the coil cross-sectional area decreases from point 2010A to point 2010B of FIG. 20 and the cross-sectional shape changes. In this example the cross-sectional area decreases variably and the shape changes from approximately circular at point 2010A to approximately a closed-arc shape at point 2010B. Other embodiments may include other cross-sectional shapes, and the cross-sectional shape and/or cross-sectional area variations may be discrete across lengthwise sections of the spring or continuously variable such as is shown in FIG. 20. Spring elements such as that shown in FIG. 20 with varying cross-sectional areas and/or shapes may be used in various embodiments similar to the spring assembly embodiments described previously herein to provide variable flexibility.

In the example of FIG. 20, the reduced cross-section of the coils due to the boring of the internal diameter, along the tapered flex section 2010, may allow the tapered flex section 2010 to bend and flex with less resistance near point 2010B than the other sections of the nested inner spring 1910 to provide varying flexibility across the spring's length. The forward-most or distal coils within tapered flex section 2010 (near point 2010B as shown in FIG. 20), where the most material has been removed, may be more flexible than those coils towards the proximal end of the tapered flex section 2010 near point 2010A. As such, an element such as a camera head, cutting tool, and the like may be coupled to this distal end and may flex or bend more.

Furthermore, while the varying sections may, in some embodiments, be discrete in cross-sectional shape, area, and/or closed or open coiled, tapering of the material removed from within the nested inner spring 1910 along the tapered flex section 2010 as shown may better provide a smooth transition in the force required to cause the nested inner spring 1910 to bend and flex. In other embodiments, material may be cut away from the outer diameter of the spring or springs in addition to or in lieu of material removed from the inner diameter of the spring or through other modifications to one or more spring elements, either external or nested within other spring elements.

In one or more exemplary embodiments, the functions, methods and processes described may be implemented in hardware, software, firmware, or any combination thereof in one or more processing element comprising a microprocessor, microcontroller, DSP, and/or other processing device along with associated non-transitory memory device(s). If implemented in software, the functions may be stored on or encoded as one or more instructions or code on a memory device such as a non-transitory computer-readable medium. Computer-readable media include computer storage media. Storage media may be any available media that can be accessed by a computer. By way of example, and not limitation, such computer-readable media can include RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

It is understood that the specific order or hierarchy of steps or stages in the processes and methods disclosed are examples of exemplary approaches. Based upon design preferences, it is understood that the specific order or hierarchy of steps in the processes may be rearranged while remaining within the scope of the present disclosure. The accompanying method claims present elements of the various steps in a sample order and are not meant to be limited to the specific order or hierarchy presented unless explicitly noted.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that the various illustrative logical blocks, modules, circuits, and algorithm steps described in connection with the embodiments disclosed herein may be implemented as electronic hardware, computer software, or combinations of both in one or more processing elements. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the disclosure.

The various illustrative logical blocks, modules, and circuits described in connection with the embodiments disclosed herein may be implemented or performed in a processing element with a general purpose processor, special purpose processor, digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine, which may be programmed to perform the specific functionality described herein, either directly or in conjunction with an external memory or memories. A processor may also be implemented as a combination of computing devices, e.g., a combination of a DSP and a microprocessor, a plurality of microprocessors, one or more microprocessors in conjunction with a DSP core, or any other such configuration.

The scope of the invention is not intended to be limited to the aspects shown herein, but is to be accorded the widest scope consistent with the language herein and accompanying drawing figures, wherein reference to an element in the singular is not intended to mean "one and only one" unless specifically so stated, but rather "one or more." Unless specifically stated otherwise, the term "some" refers to one or more. A phrase referring to "at least one of" a list of items refers to any combination of those items, including single members. As an example, "at least one of: a, b, or c" is intended to cover: a; b; c; a and b; a and c; b and c; and a, b and c.

The previous description of the disclosed aspects is provided to enable any person skilled in the art to make or use embodiments of the present invention. Various modifications to these aspects will be readily apparent to those skilled in the art, and the generic principles defined herein may be applied to other aspects without departing from the spirit or scope of the invention. For example, various ways of providing varying spring element and spring assembly flexibility as described previously herein may be combined in alternate configurations to those specifically recited herein and shown in the corresponding drawing figures such as by combining various aspects described herein in alternate configurations. In one example, springs of varying cross-section, and/or varying lengthwise material properties, and/or varying lengthwise cross-section, and/or varying diameter, and/or varying open and closed coil configurations, and the like may be combined in one or more elements, and may be configured in the same way as described previously herein or may be varied in nested elements to provide alternate spring assemblies. Any of various other combinations may also be used in additional embodiments. Accordingly, the disclosure is not intended to be limited to the aspects shown herein but is to be accorded the widest scope consistent with the appended Claims and their equivalents.

We claim:

1. A pipe inspection system apparatus, comprising:
a push-cable having a proximal end and a distal end;
a spring assembly disposed about the distal end of the push-cable, the spring assembly comprising:
an elongate outer coiled spring having a variable flexibility along its length, wound in a first direction, the outer coiled spring having a plurality of lengthwise sections including at least a front section having a first cross-sectional area and a rear section having a second cross-sectional area different from the first cross-sectional area; and
an inner coiled spring wound in a second direction opposite to the first direction, wherein the inner coiled spring is shorter than the outer coiled spring and the inner coiled spring is nested within at least a portion of the outer coiled spring; and
one or more connecting wires disposed at least partially within the spring assembly;
wherein the front section of the outer coiled spring has a higher flexibility than the rear section.

2. The apparatus of claim 1, further comprising a camera head including an imaging element, a processing element, and optics wherein the camera head is mechanically coupled to the spring assembly and electrically coupled to the push-cable through the connecting wires.

3. The apparatus of claim 2, wherein the camera head further includes one or more lighting elements powered through the connecting wires.

4. The apparatus of claim 1 further comprising a sonde disposed within the outer coiled spring.

5. The apparatus of claim 1, wherein coils of the front section has a different cross-sectional coil shape than coils of the rear section.

6. The apparatus of claim 1, wherein the connecting wires include signal wires.

7. The apparatus of claim 1, further comprising a push-cable connector element coupled to a proximal end of the outer coiled spring to couple the push-cable to the spring assembly, the push-cable connector element includes outer spring threads having a threaded element shaped to mate with a corresponding coil threading of the outer coiled spring and inner spring threads having a threaded element shaped to mate with a corresponding coil threading of the inner coiled spring.

8. The apparatus of claim 1, further comprising an inner spring mounting element disposed within the outer coiled spring, the inner mounting element including a threaded element shaped to mate with a corresponding coil threading of the inner coiled spring.

9. The apparatus of claim 1, wherein the front section includes a plurality of coils of a first coil diameter and the rear section includes a plurality of coils of a second diameter different from the first coil diameter.

* * * * *